US008043804B2

(12) United States Patent
Gu

(10) Patent No.: US 8,043,804 B2
(45) Date of Patent: Oct. 25, 2011

(54) DBC1, A NOVEL NATIVE INHIBITOR OF ANTI-AGING PROTEIN SIRT1

(75) Inventor: Wei Gu, Paramus, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 106 days.

(21) Appl. No.: 12/154,503

(22) Filed: May 23, 2008

(65) Prior Publication Data

US 2009/0036375 A1  Feb. 5, 2009

Related U.S. Application Data

(60) Provisional application No. 60/931,613, filed on May 23, 2007.

(51) Int. Cl.
*C12Q 1/68* (2006.01)
(52) U.S. Cl. ........................................................ 435/6
(58) Field of Classification Search .................. None
See application file for complete search history.

(56) References Cited

U.S. PATENT DOCUMENTS

| 4,690,918 | A | 9/1987 | Beppu et al. |
| 7,241,743 | B2 | 7/2007 | Gu et al. |
| 2002/0183388 | A1 | 12/2002 | Gudas et al. |
| 2003/0207325 | A1 | 11/2003 | Guarente et al. |
| 2004/0029134 | A1 | 2/2004 | Gu et al. |
| 2005/0037345 | A1 | 2/2005 | Inazawa et al. |
| 2008/0119434 | A1 | 5/2008 | Gu et al. |

FOREIGN PATENT DOCUMENTS

| WO | WO/02/102981 | 12/2002 |
| WO | WO/2004/053142 | 6/2004 |

OTHER PUBLICATIONS

Oct. 6, 2004 Office Action issued from the United States Patent and Trademark Office in connection with U.S. Appl. No. 10/172,706.
Apr. 29, 2005 Final Office Action issued from the United States Patent and Trademark Office in connection with U.S. Appl. No. 10/172,706.
Dec. 29, 2005 Final Office Action issued from the United States Patent and Trademark Office in connection with U.S. Appl. No. 10/172,706.
Sep. 6, 2006 Office Action issued from the United States Patent and Trademark Office in connection with U.S. Appl. No. 10/172,706.
Mar. 5, 2007 Notice of Allowability issued from the United States Patent and Trademark Office in connection with U.S. Appl. No. 10/172,706.
Aug. 17, 2006 Office Action issued from the United States Patent and Trademark Office in connection with U.S. Appl. No. 10/313,203.
Jan. 24, 2007 Final Office Action issued from the United States Patent and Trademark Office in connection with U.S. Appl. No. 10/313,203.
Nov. 15, 2005 Office Action issued from the United States Patent and Trademark Office in connection with U.S. Appl. No. 10/313,203.
Sep. 30, 2009 Office Action issued from the United States Patent and Trademark Office in connection with U.S. Appl. No. 11/825,944.
PCT International Search Report issued Dec. 8, 2008 in connection with PCT International Application No. PCT/US2003/38658, filed on Dec. 4, 2003.
PCT International Search Report issued Jul. 23, 2003 in connection with PCT International Application No. PCT/US2003/38658, filed on Dec. 4, 2003.
PCT International Preliminary Examination Report issued Feb. 22, 2004 in connection with PCT International Application No. PCT/US2002/29019, filed on Jun. 14, 2002.
Jan. 6, 2005 Amendment in Response to Oct. 6, 2004 Office Action issued in connection with U.S. Appl. No. 10/172,706.
Jul. 29,2005 Amendment in Response to Apr. 29, 2005 Final Office Action issued in connection with U.S. Appl. No. 10/172,706.
Jun. 29, 2006 Communication in Response to Dec. 29, 2005 Final Office Action issued in connection with U.S. Appl. No. 10/172,706.
Dec. 6, 2006 Amendment in Response to Sep. 6, 2006 Office Action issued in connection with U.S. Appl. No. 10/172,706.
Nov. 17, 2006 Amendment in Response to Aug. 17, 2006 Office Action issued in connection with U.S. Appl. No. 10/313,203.
Gu, W. et al., (1999) "A Novel Human SRB/MED-Containing Cofactor Complex SMCC, Involved in Transcription Regulation." Molecular Cell, vol. 3, Issue 1, pp. 97-108.
Gu, W. et al., (1997) "Activation of p53 Sequence-Specific DNA Binding by Acetylation of the p53 C-Terminal Domain." Cell 90(4):595-606.
Gu, W. et al., (1997) "Synergistic Activation of Transcription by CBP and p53." Nature 387, 819-823.
Guarente, L., (2000) "Sir2 links Chromatin Silencing, Metabolism, and Aging." Genes Dev. 14, 1021-1026.
Landry, J., et al., (2000) "The Silencing Protein SIR2 and its Homologs are NAD-Dependent Protein Deacetylases." Proc. Natl. Acad. Sci. U.S.A. 97, 5807-5811.
Langley, E., et al., (2002) "Human SIR2 Deacetylates p53 and Antagonizes PML/p53-Induced Cellular Senescence." The EMBO Journal. vol. 21, No. 10, 2383-2396.

(Continued)

Primary Examiner — Tracy Vivlemore
(74) Attorney, Agent, or Firm — John P. White; Cooper & Dunham LLP

(57) ABSTRACT

A novel complex is identified between the NAD-dependent deacetylase, SIRT1 and its novel inhibitor, DBC1. Provided herein are methods to identify a compound that inhibits the complexation between SIRT1 and DBC1. Exemplary methods comprise contacting either the complexation between DBC1 and SIRT1 with an agent being tested for its ability to inhibit the complexation between SIRT1 and DBC1. Also, provided are methods to identify a compound that increases the complexation between SIRT1 and DBC1. Exemplary methods comprise contacting either the complexation between DBC1 and SIRT1 with an agent being tested for its ability to increase the complexation between SIRT1 and DBC1. Further, methods are provided to increase or decrease SIRT1 activity by contacting the complexation between SIRT1 and DBC1 with a peptide that either decreases or increases the complexation between SIRT1 and DBC1. Further, methods are provided for the treatment of patients suffering from diseases including metabolic diseases including obesity and diabetes, and neurodegenerative disorders including Alzheimer's disease and Huntington's disease using compounds that inhibit the complexation between SIRT1 and DBC1.

11 Claims, 24 Drawing Sheets

OTHER PUBLICATIONS

Lin, S.J., et al., (2000) "Requirement of NAD and SIR2 for Life-Span Extension by Calorie Restriction in *Saccharomyces cerevisiae*." Science 289, 2126-2128.

Luo, J. et al., (Oct. 19, 2001) "Negative Control of p53 by Sir2alpha Promotes Cell Survival Under Stress." Cell. vol. 107, No. 2, pp. 137-148.

Vaziri, H., et al., (2000) "hSIR2SIRT1 Functions as an NAD-Dependent p53 Deacetylase." Cell. (107)149-159.

Baur, JA, et al. (2006) "Resveratrol improves health and survival of mice on high-calorie diet." Nature, 444:337-342.

Baur, JA & Sinclair, D.A. (2006) "Therapeutic potential of Resveratrol: the in vivo evidence." Nat Rev Drug Discv, 5:493-506.

Bordone, L & Guarente, L (2005) "Calorie restriction, SIRT1 and metabolism: understanding longevity." Nat Rev Mol Cell Biol,. 6:298-305.

Brunet, A, et al. (2004) "Stress-dependent regulation of FOXO transcription factors by the SIRT1 deacetylase." Science, 303:2011-5.

Chen, D, et al., (2005) "Increase in activity during calorie restriction requires SIRT1." Science, 310:1641.

Chen, WY, et al. (2005) "Tumor suppressor HIC1 directly regulates SIRT1 to modulate p53-dependent DNA-damage responses." Cell, 123:437-48.

Cheng, HL, et al. (2003) "Developmental defects and p53 hyperacetylation in Sir2 homolog (SIRT1)-deficient mice." Proc Natl Acad Sci USA, 100:10794-9.

Cohen, HY, et al. (2004) "Acetylation of the C terminus of Ku70 by CBP and PCAF controls Bax-mediated apoptosis." Mol Cell, 13:627-38.

Greene, WC & Chen, LF (2004) "Regulation of NF-kappaB action by reversible acetylation." Novartis Found Symp, 259:208-222.

Kaeberlein, M, et al., (1999) "The SIR2/3/4 Complex and SIR2 Alone Promote Longevity in *Saccharomyces cerevisiae* by Two Different Mechanisms." Genes Dev, 13:2570-2580.

Kitamura, YI, et al. (2005) "FoxO1 protects against pancreatic beta cell failure through NeuroD and MafA induction." Cell Metab, 2:153-63.

Luo, J, et al. (2000) "Deacetylation of p53 modulates its effect on cell growth and apoptosis." Nature, 408:377-381.

Motta, MC, et al. (2004) "Mammalian SIRT1 represses forkhead transcription factors." Cell, 116:551-63.

Nikolaev ,et al., (Jan. 10, 2003) "Parc: Cytoplasmic Anchor for p53," Cell, 112: 29-40.

North, BJ & Verdin, E (2004) "SIRTuins: Sir2-related NAD-dependent protein deacetylases." Genome Biol, 5:224.

Picard, F, et al. (2004) "SIRT1 promotes fat mobilization in white adipocytes by repressing PPAR-gamma." Nature, 429:771-776.

PRI Database, National Center for Biotechnology Information, National Library of Medicine, NIH (Bethesda, MD, U.S.A.) Accession No. AJ318215. Jun. 2002.

Rodgers, JT, et al. (2005) "Nutrient control of glucose homeostasis through a complex of PGC-1alpha and SIRT1." Nature, 434:113-8.

Rogina, B & Helfand, SL (2004) "Sir2 mediates longevity in the fly through a pathway related to calorie restriction." Proc Natl Acad Sci USA, 101:15998-16003.

Tang, BL & Chua CE (Feb. 2007) "SIRT1 and neuronal diseases." Mol Aspects Med, 29:187-200.

Tissenbaum, HA, et al., (2001) "Increased Dosage of a sir-2 Gene Extends Lifespan in *Caenorhabditis elegans*." Nature, 410:227-230.

Yeung, F, et al. (2004) "Modulation of NF-kappaB-dependent transcription and cell survival by the SIRT1 deacetylase." EMBO J, 23:2369-80.

Figure 18
A. Modified Sir2 BAC
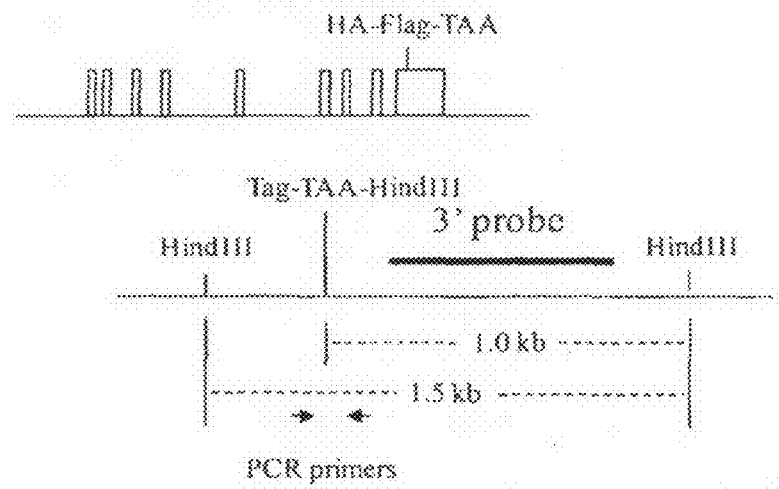
B. Genotyping by Southern Blot
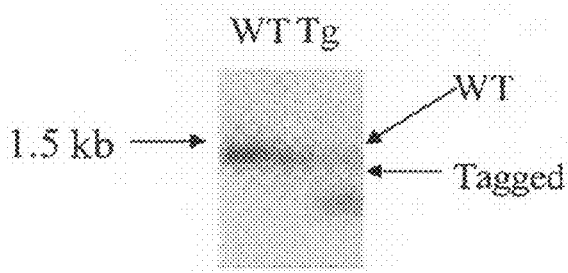
C. Genotyping by PCR
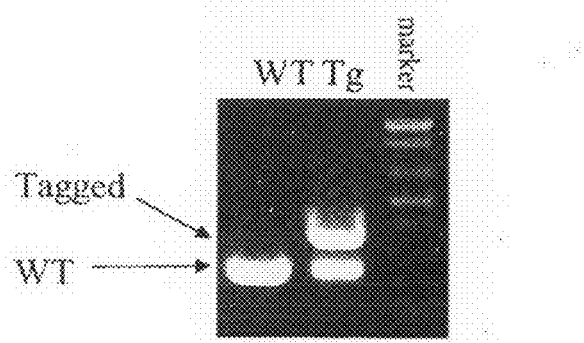

Figure 19
A. Western blot of extracts from testis
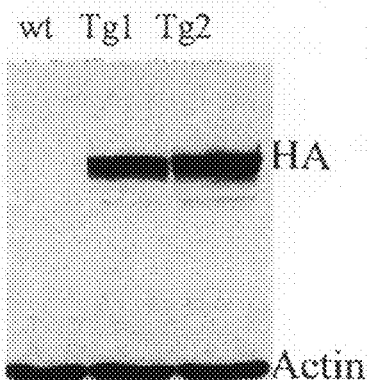
B. Western blot using anti Sir2 antibody
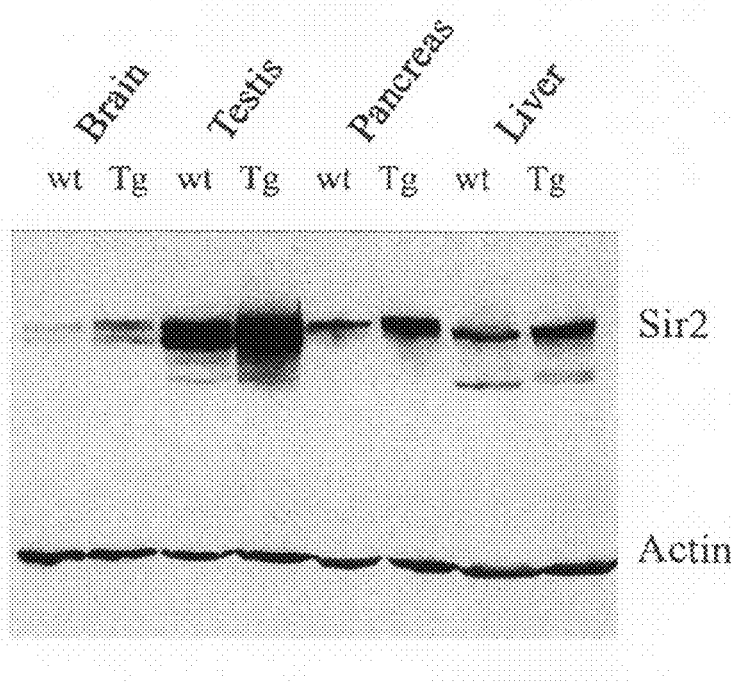

Figure 21
A.   WT   WT   Tg   Tg
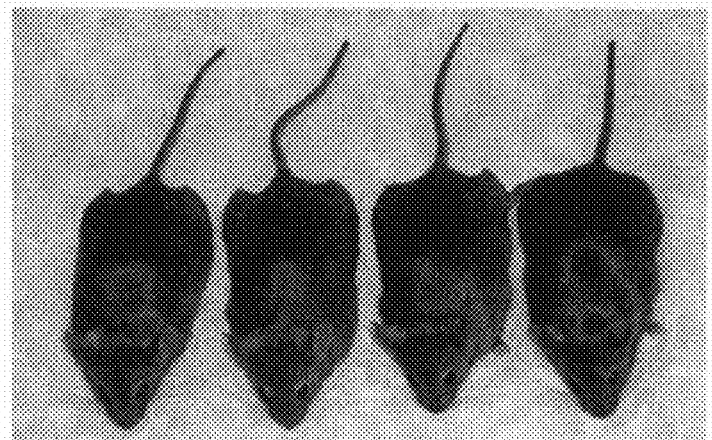
B.
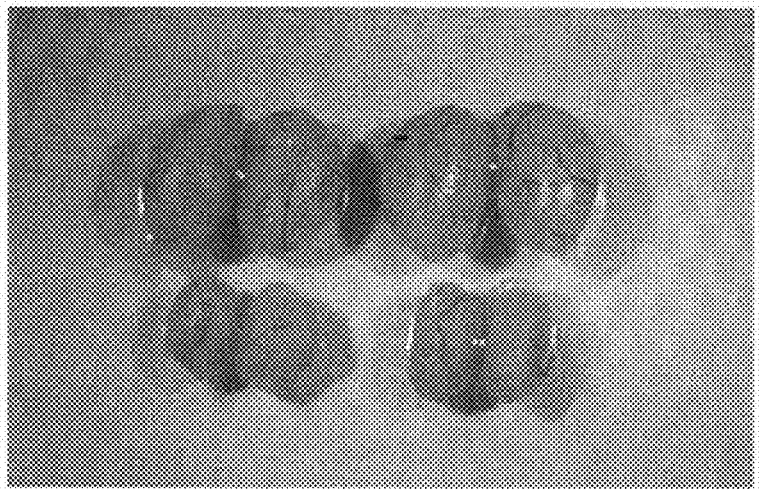

Figure 23
A
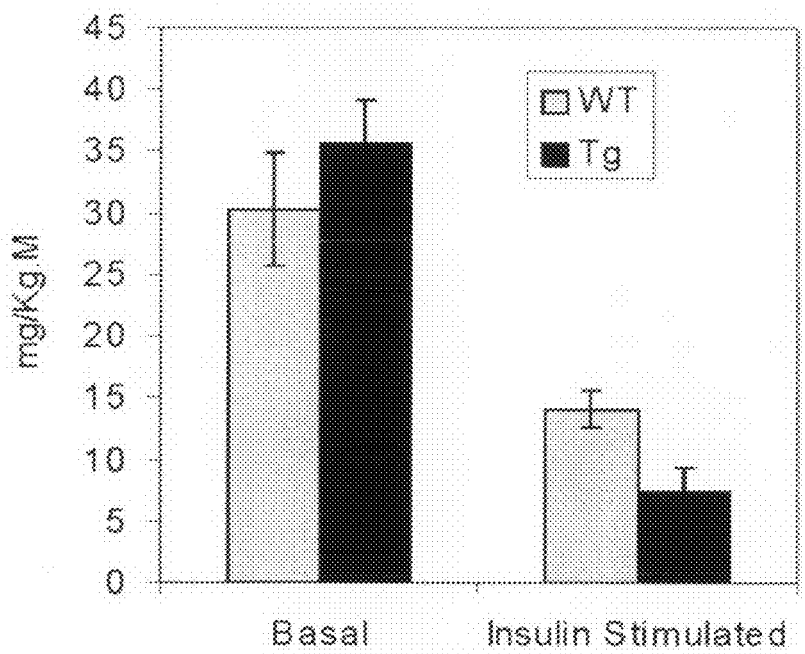
Hepatic Glucose Production
B
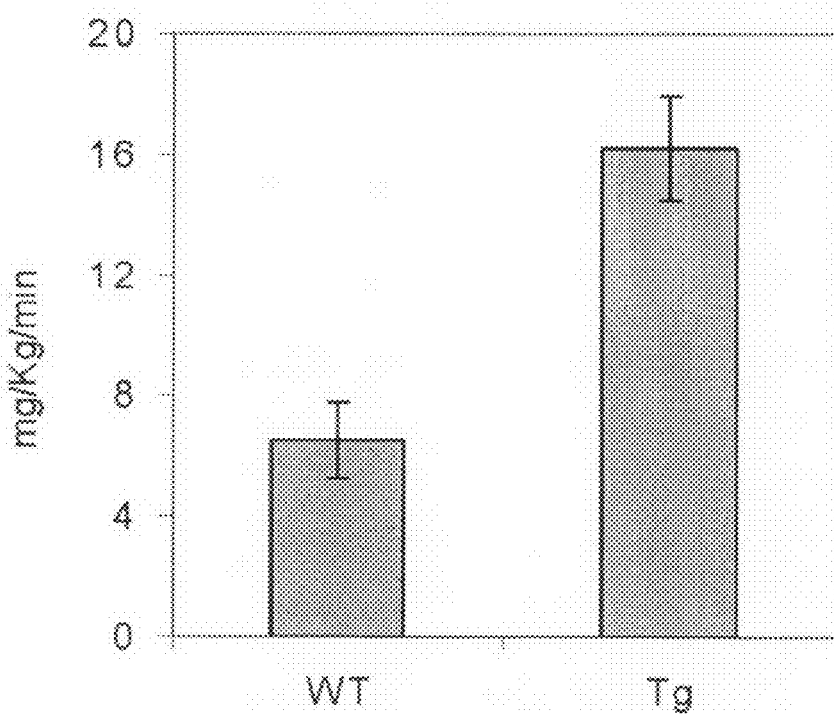
Glucose Infusion Rate

DBC1, A NOVEL NATIVE INHIBITOR OF ANTI-AGING PROTEIN SIRT1

This application claims the benefit of U.S. Provisional Application No. 60/931,613, filed May 23, 2007, the contents of which are hereby incorporated by reference into this application.

The work disclosed herein was made with government support under grant NIH RO1 CA098821 from the National Institutes of Health. Accordingly, the U.S. Government has certain rights in this invention.

Throughout this application, various publications are referenced in parentheses the first author's last name and year of publication. Citations for these references may be found at the end of the specification immediately preceding the claims. The disclosures of these publications in their entireties are hereby incorporated by reference into this application to more fully describe the state of the art to which this invention pertains.

BACKGROUND

The Sir2 (silent information regulator 2) proteins are an evolutionarily-conserved family of class III histone deacetylases (HDACs) (Bordone, et al., 2005; North et al., 2004; Baur, et al., 2006). Unlike class I and II HDACs, the catalytic activity of the Sir2 family requires the cofactor NAD, a key product of cellular metabolism. In yeast, Sir2 acts as a transcriptional repressor by deacetylating histones and its homologues have also been found to promote longevity in yeast, flies, and worms (Kaeberlein, 1999; Rogina and Helfand, 2004; Tissenbaum, 2001) indicating that it is an anti-aging gene of broad significance. In mammals, there are seven members of the Sir2 family, termed SIRTuins (SIRTs), of which SIRT1 is the closest homolog of yeast Sir2. In early studies, it was found that the tumor suppressor p53 can be dynamically regulated by acetylation and deacetylation (Gu, et al., 1997; Luo, et al., 2000; it was subsequently found that SIRT1 promotes cell survival by inhibiting apoptosis and deacetylation of p53 (Luo, et al., 2001; Langley, et al., 2001; Vaziri, et al., 2001). These results were further supported by the fact that p53 hyperacetylation and increased radiation-induced apoptosis were observed in SIRT1-deficient mice (Cheng, et al., 2003).

Nevertheless, SIRT1-mediated regulation is also implicated in p53-independent pathways (Motta, et al., 2004; Brunet, et al., 2004; Kitamura, et al., 2005; Cheng et al, 2003, Chen, et al, 2005; Yeung, et al., 2004; Greene & Chen, 2004; Rodgers, et al., 2005; Cohen, et al., 2004). For example, FOXO family proteins, RelA/p65 subunit of NF-κB and Ku70 are substrates of SIRT1 and deacetylation of these factors is involved in the stress response under different cellular contexts.

Moreover, recent studies indicate that SIRT1 directly interacts with PPAR-γ and PGC-1α and modulates metabolic responses (Bordone, et al., 2005; North, et al., 2004; Baur, et al., 2006; Rodgers, et al., 2005). SIRT1 is expressed in white adipose tissue (WAT) and its levels rise in calorie restricted animals (Cohen, 2004). Moreover, SIRT1 has been shown to inhibit adipogenesis in white adipose tissue and promote fat disposal in fully differentiated white adipocytes (Picard, 2004). SIRT1 binds to the negative cofactors NCoR and SMART, and may thus inhibit the activity of the proadipogenic nuclear receptor, PPAR-γ. These studies validate the importance of the deacetylase activity of SIRT1, but it remains unclear how SIRT1-mediated deacetylation is controlled in vivo.

Further, induction of SIRT1 expression also attenuates neuronal degeneration and death in animal models of Alzheimer's disease and Huntington's disease (Tang, et al., 2007).

SUMMARY OF INVENTION

Provided herein are methods for identifying a compound which inhibits the novel complexation between the SIRT1 protein and the DBC1 protein by contacting the complexation with an agent being tested for its ability to inhibit the complexation between the two proteins and measuring the increase in unbound SIRT1 or the decrease in the complexation between SIRT1 protein and DBC1 protein as compared to the control sample. If the level of unbound SIRT1 protein increases of the level of the complexation between SIRT1 and DBC1 decreases, then the agent being tested inhibits the complexation.

Also provided herein are methods the increase the complexation between the SIRT1 protein and DBC1 protein by contacting the complexation with an agent being tested for its ability to increase complexation between SIRT1 protein and DBC1 protein and measuring the decrease in unbound SIRT1 or the increase in complexation between SIRT1 and DBC1 as compared to the control sample. If the level of unbound SIRT1 decreases or the level of complexation between SIRT1 and DBC1 increases, then the agent being tested increases the complexation.

Also provided herein is a method for decreasing SIRT1 activity by contacting the complexation between SIRT1 and DBC1 with an agent which inhibits SIRT1.

Also provided herein is a method for increasing SIRT1 activity by contacting the complexation between SIRT1 and DBC1 with an agent which inhibits DBC1.

Also provided here is a method for treating a patient suffering from a disease including metabolic and neurodegenerative diseases by administering to the patient a compound which inhibits the complexation of DBC1 and SIRT1 in an amount therapeutically effective to treat the patient.

BRIEF DESCRIPTION OF THE FIGURES

FIG. 18. Generation of SIR2 BAC and resulting SIR2 transgenic mouse. (a) Schematic representation of the Southern blot method and PCR method used to genotype the SIR2 transgenic mice. (b) Southern blot depicting the presence of the Sir2 transgene and endogenous Sir2 in transgenic mice (see lane marked 'Tg') as compared to wildtype mice, which only have the endogenous Sir2 (see lane marked 'WT'). (c) PCR method used to detect the presence of the Sir2 transgene and endogenous SIR2 in transgenic mice (see lane marker 'Tg') as compared to wildtype mice which only have endogenous Sir2 (see lane marked 'WT').

FIG. 19. Confirmation of Sir2 expression pattern in tissues of transgenic mice. (a) Cellular extracts made from testis from wildtype (wt), and Sir2 transgenic mice (Tg1 and Tg2) were processed for Western blotting and probed for transgenic HA-tagged Sir2 using an anti-HA antibody. HA-tagged transgenic Sir2 was detected only in the testis cell extracts from transgenic mice Tg1 and Tg2. An anti-actin western blot was included was a loading control. (b) Brain, testis, pancreas and liver tissues from wildtype and Sir2 transgenic mice were processed for Western blotting and probed for Sir2 using an anti-Sir2 antibody. The increase in Sir2 levels in the tissues from transgenic mice (Tg) as compared to wildtype mice (wt) could be determined using densitometry.

FIG. 21 shows that the Sir2 BAC transgenic mice do not show any significant difference in total body mass and percent body fat composition (a) and no significant difference was observed for internal organs (b).

FIG. 23 shows that insulin stimulated inhibition of hepatic glucose production in greater in Sir2 transgenic mice and non transgenic mice (a) and glucose infucion rates are much higher in Sir2 transgenic mice than non-transgenic mice (b).

DETAILED DESCRIPTION OF THE INVENTION

Figure 1:
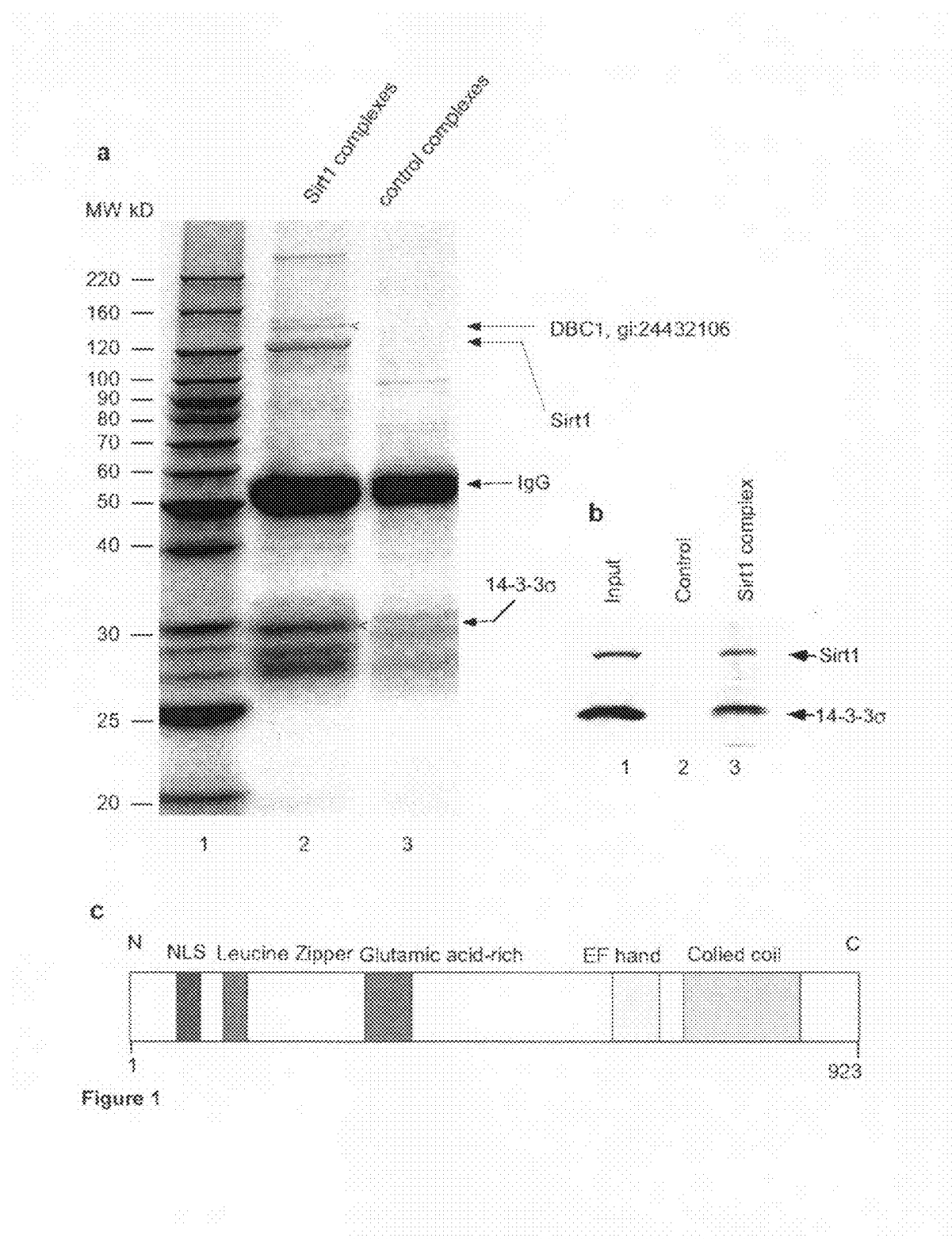
FIG. 1. Identification of DBC1 as a major component of the SIRT1 complexes in human cells. (a) Colloidal-blue staining of affinity-purified SIRT1 complexes from HeLa extracts with the α-SIRT1 antibody column (lane 2) and a control elute from the same extract with a control antibody column (lane 3). Specific SIRT1 interacting proteins were analyzed by mass spectrometry. (b) Western Blot of input (lane 1), control IP (lane 2) and α-SIRT1 antibody IP (lane 3) for the known SIRT1 interacting protein 14-3-3σ (lower panel) and SIRT1 (upper panel) to verify specificity of the analyzed SIRT1 complex. (c) Schematic representation of the DBC1 protein.

This disclosure relates a novel isolated complexation between the SIRT1 protein and the DBC1 protein and methods for identifying compounds which modulate this complexation, either by inhibiting the complexation or increasing the complexation. This disclosure also relates a method for modulating SIRT1 activity using peptides to increase or decrease SIRT1 activity.

In one embodiment, this disclosure features a method for identifying a compound which inhibits the complexation between SIRT1 and DBC1 by contacting the complexation with the agent being tested and determining the increase in unbound SIRT1 or the decrease in the complexation between SIRT1 and DBC1 as compared to the control sample. If the level of increase in unbound SIRT1 or the level of decrease in complexation between SIRT1 and DBC1 is different from the control sample then the agent being tested inhibits the complexation. In one embodiment, the agent being tested for its ability to inhibit complexation is tested in vitro. In a further embodiment, the agent being tested is a peptide. In a still further embodiment the peptide hybridizes with the target under stringent conditions. In a still further embodiment, the peptide is comprised of amino acids 210 to 500 of the SIRT1 protein.

In vitro assays can be used to determine the difference in levels of inhibition of complexation. In one embodiment, the difference is determined by differential centrifugation; chromatography (gel filtration chromatography, ion-exchange chromatography); electrophoresis; immunoprecipitation; pulldown assays, ELISA assays; fluorescence energy transfer, surface plasmon resonance; or in vitro tubulin deacetylation assays.

In another embodiment, the agent being tested for its ability to inhibit complexation between SIRT1 and DBC1 is tested on a cell. In a further embodiment, the agent is inside the cell. In a still further embodiment, the agent is an siRNA or an shRNA.

In another embodiment, the agent being tested for its ability to inhibit complexation between SIRT1 and DBC1 is tested on a cell. In a further embodiment, the agent is outside the cell and has a cascade effect.

The cell being contacted with the agent being tested for its ability to inhibit complexation between SIRT1 and DBC1 may be a yeast cell or a human osteosarcoma U2Os cell.

Cell based assays can be used to determine the difference in levels of inhibition of complexation. In one embodiment, the difference is determined by yeast two hybrid, adipocyte differentiation assay, or a deacetylation assay.

In one embodiment, this disclosure features a method for identifying a compound which increases the complexation between SIRT1 and DBC1 by contacting the complexation with the agent being tested and determining the decrease in unbound SIRT1 or the increase in the complexation between SIRT1 and DBC1 as compared to the control sample. If the level of decrease in unbound SIRT1 or the level of increase in complexation between SIRT1 and DBC1 is different from the control sample then the agent being tested increases the complexation. In one embodiment, the agent being tested for its ability to increase complexation is tested in vitro.

In vitro assays can be used to determine the difference in levels of increase in complexation. In one embodiment, the difference is determined by differential centrifugation; chromatography (gel filtration chromatography, ion-exchange chromatography); electrophoresis; immunoprecipitation; pulldown assays, ELISA assays; fluorescence energy transfer, surface plasmon resonance; or in vitro tubulin deacetylation assays.

In another embodiment, the agent being tested for its ability to increase complexation between SIRT1 and DBC1 is tested on a cell. In a further embodiment, the agent is inside the cell.

In another embodiment, the agent being tested for its ability to increase complexation between SIRT1 and DBC1 is tested on a cell. In a further embodiment, the agent is outside the cell and has a cascade effect.

The cell being contacted with the agent being tested for its ability to increase complexation between SIRT1 and DBC1 may be a yeast cell or a human osteosarcoma U2Os cell.

Cell based assays can be used to determine the difference in levels of increase in complexation. In one embodiment, the difference is determined by yeast two hybrid, adipocyte differentiation assay, or a deacetylation assay.

This disclosure also describes a method for increasing SIRT1 activity by contacting the complexation between SIRT1 and DBC1 with an agent which inhibits DBC1 activity. In one embodiment, the agent is a peptide. In a further embodiment, the peptide hybridizes to DBC1 under stringent conditions. In a still further embodiment, the peptide is comprised of amino acids 210 to 500 of the SRT1 protein.

Also described in this disclosure is a method for decreasing SIRT1 activity by contacting the complexation between SIRT1 and DBC1 with an agent that inhibits SIRT1. In one embodiment, the agent is a peptide. In a further embodiment, the peptide hybridizes to SIRT1 under stringent conditions. In a still further embodiment, the peptide is comprised of amino acids 1 to 399 of the DBC1 protein.

In one embodiment, this disclosure features a method of treating a patient suffering from metabolic diseases including insulin resistance, diabetes, obesity, impaired glucose tolerance, high blood cholesterol, hyperglycemia, dyslipidemia and hyperlipidemia, and neurodegenerative diseases including Parkinson's Disease, Huntington's Disease, Alzheimer's Disease, amyotrophic lateral sclerosis (ALS), dementia, multiple sclerosis comprising administering to the patient a compound which inhibits the complexation of DBC1 and SIRT1 in an amount therapeutically effective to treat the patient.

DEFINITIONS

"SIRT1" shall refer to Silencing mating type information regulator 2 homolog and is a member of the SIRTuin deacetylase protein family. The amino acid sequence of SIRT1 may be found at Genbank Accession number NP_08509. SIRT1 is the human homolog of the yeast Sir2 protein and exhibits NAD-dependent deacetylase activity.

"DBC1" shall refer to Deleted in Breast Cancer 1 protein. The amino acid sequence of DBC1 may be found at Genbank Accession number Gi:24432106.

A "carrier" shall mean a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body.

"Pharmaceutically acceptable carriers" are well known to those skilled in the art and include, but are not limited to, 0.01-0.1M and preferably 0.05M phosphate buffer, phosphate-buffered saline (PBS), or 0.9% saline. Additionally, such pharmaceutically acceptable carriers may include, but are not limited to, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a non-toxic surfactant, for example, esters or partial esters of C6 to C22 fatty acids or natural glycerides, and a propellant. Additional carriers such as lecithin may be included to facilitate intranasal delivery. Preservatives and other additives, such as, for example, antimicrobials, antioxidants, chelating agents, inert gases, and the like may also be included with all the above carriers.

Adjuvants are formulations and/or additives that are routinely combined with antigens to boost immune responses. Suitable adjuvants for nucleic acid based vaccines include, but are not limited to, Quil A, imiquimod, resiquimod, interleukin-12 delivered in purified protein or nucleic acid form, short bacterial immunostimulatory nucleotide sequences such as CpG-containing motifs, interleukin-2/Ig fusion proteins delivered in purified protein or nucleic acid form, oil in water micro-emulsions such as MF59, polymeric microparticles, cationic liposomes, monophosphoryl lipid A, immunomodulators such as Ubenimex, and genetically detoxified toxins such as *E. coli* heat labile toxin and cholera toxin from *Vibrio*. Such adjuvants and methods of combining adjuvants with antigens are well known to those skilled in the art.

Adjuvants suitable for use with protein immunization include, but are not limited to, alum; Freund's incomplete adjuvant (FIA); saponin; Quil A; QS-21; Ribi Detox; monophosphoryl lipid A (MPL) adjuvants such as Enhanzyn™; nonionic block copolymers such as L-121 (Pluronic; Syntex SAF); TiterMax Classic adjuvant (block copolymer, CRL89-41, squalene and microparticulate stabilizer; Sigma-Aldrich); TiterMax Gold Adjuvant (new block copolymer, CRL-8300, squalene and a sorbitan monooleate; Sigma-Aldrich); Ribi adjuvant system using one or more of the following: monophosphoryl lipid A, synthetic trehalose, dicorynomycolate, mycobacterial cell wall skeleton incorporated into squalene and polysorbate-80; Corixa); RC-552 (a small molecule synthetic adjuvant; Corixa); Montanide adjuvants (including Montanide IMS111X, Montanide IMS131x, Montanide IMS221x, Montanide IMS301x, Montanide ISA 26A, Montanide ISA206, Montanide ISA 207, Montanide ISA25, Montanide ISA27, Montanide ISA28, Montanide ISA35, Montanide ISA50V, Montanide ISA563, Montanide ISA70, Montanide ISA 708, Montanide ISA740, Montanide ISA763A, and Montanide ISA773; Seppic Inc., Fairfield, N.J.); and N-Acetylmuramyl-L-alanyl-D-isoglutamine hydrate (Sigma-Aldrich). Methods of combining adjuvants with antigens are well known to those skilled in the art.

"Agent" shall mean any chemical entity, including, without limitation, a glycomer, a protein, an antibody, a lectin, a nucleic acid, a small molecule, a phytoalexin, a flavone, a stilbene, a flavanone, and isoflavone, a catechin, a tannin, an anthocyanidin, a quinoxaline or a sphingolipid and any combination thereof, as well as biological entities such as exosomes or liposomes. Examples of possible agents include, but are not limited to, monoclonal antibody, a ribozyme, a DNAzyme and an siRNA molecule.

"Inhibit complexation" shall mean that the existing complexation between SIRT1 and DBC1 is disrupted or the complexation between SIRT1 and DBC1 is inhibited by preventing either or both proteins from forming the complexation.

"Cascade effect" as used herein shall refer to the binding of an agent to a receptor or ligand on the surface of a cell such that the binding stimulates downstream signaling events culminating in the inhibition of the complexation between SIRT1 and DBC1.

"siRNA" shall mean small interfering ribonucleic acid, e.g. a short (e.g. 21-23 nt) RNA duplex which can elicit an RNA interference (RNAi) response in a mammalian cell siRNAs may be blunt ended or have mono, di or trinucleotide 3' overhangs.

"shRNA" shall mean short hairpin interfering ribonucleic acid containing a double stranded base-paired segment, each strand of which is contiguous at one of its ends with a loop (or non-base-paired) segment and which can be processed in a cell into a siRNA. By way of example, the base-paired segment can be 19 base-pairs in length.

A 'peptide' shall mean a sequence of amino acids at least 15 residues long which hybridizes to the target protein under high stringency conditions. The peptide can be a decoy peptide which hybridizes to either SIRT1 or DBC1 under high stringency conditions to prevent or disrupt complexation formation between DBC1 and SIRT1. In other embodiments, the peptide is derived from the DBC1 binding domain of SIRT1 which spans amino acid residues 210 to 500 of SIRT1 or any smaller portion of the DBC1 binding domain of the SIRT1 protein which hybridizes to DBC1 under high stringency conditions. In alternative embodiments, the peptide is derived from SRT1 binding domain of the DBC1 protein which spans amino acids 1 to 399 or any smaller portion of the SRT1 binding domain of the DBC1 peptide which hybridizes to SIRT1 under high stringency conditions.

"Amino acid residue" shall mean one of the individual monomer units of a peptide chain, which result from at least two amino acids combining to form a peptide bond.

"Amino acid" shall mean an organic acid that contains both a basic amino group, an acidic carboxyl group and an R group.

"Neurodegenerative diseases" refers to a wide range of diseases and disorders of the central and peripheral nervous system including, for example, Parkinson's Disease, Huntington's Disease, Alzheimer's Disease, amyotrophic lateral sclerosis (ALS), dementia, multiple sclerosis and other diseases and disorders associated with neuronal cell death.

"Metabolic diseases" refers to a wide range of diseases and disorders of the endocrine system including, for example, insulin resistance, diabetes, obesity, impaired glucose tolerance, high blood cholesterol, hyperglycemia, dyslipidemia and hyperlipidemia.

"Administering" an agent can be effected or performed using any of the various methods and delivery systems known to those skilled in the art. The administering can be performed, for example, intravenously, orally, nasally, via the cerebrospinal fluid, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

As used herein, a "therapeutically effective" amount is an amount of a substance effective to treat, ameliorate or lessen a symptom or cause of a given pathological condition in a subject suffering therefrom to which the substance is to be administered.

In Vitro Assays

Cell free assays to determine the increase in unbound SIRT1 or the decrease in the complexation of SIRT1 and DBC1 can be conducted in liquid phase. In such an assay the reaction products are separated from unreacted components, by any number of standard techniques including, without limitation: differential centrifugation (for example, see Rivas, G., and Minton A. P., (1993) *Trends Biochem Sci* 18:284-287); chromatography (gel filtration chromatography, ion-exchange chromatography; electrophoresis (Ausubel, F. et al. eds., (1999) *Current Protocols in Molecular Biology*, J. Wiley: New York); and immunoprecipitation (Ausubel, F. et al. eds., (1999) *Current Protocols in Molecular Biology*, J. Wiley: New York).

Another useful assay to determine the disruption of molecular interactions between two proteins utilizes fusion proteins where the addition of a domain allows SIRT1 or both SIRT1 and DBC1 to be bound to a matrix. For example, glutathione-S-transferase-SIRT1 or glutathione-S-transferase-DBC1 can be absorbed onto glutathione sepharose beads (Sigma, St. Louis, Mo.) or glutathione derivatized microtiter plates and then combined with either untagged SIRT1 or untagged DBC1 under conditions that are conducive to complex formation (for example, at physiological conditions for salt and pH). Following incubation, the beads or the microtiter plates are washed to remove any unbound components. Following washing, the samples are treated with the compound being tested for its ability to disrupt the complexation between SIRT1 and DBC1 and the amount of unbound SIRT1 or DBC1 measured using standard techniques. This assay can also be performed using other methods to immobilize the protein onto the surface of microtiter well including conjugation of biotin and streptavidin to either SIRT1 or DBC1. Biotinylated SIRT1 and biotinylated DBC1 can be prepared from biotin-NHS (N-hydroxy-succinimide) using commercially available biotinylation kits (pierce Chemicals, Rockford, Ill.), and immobilized on streptavidin-coated microtiter plates (Pierce Chemical).

To perform the assay to test the ability of test compounds to disrupt the interaction between immobilized SIRT1 and non-absorbed DBC1 or immobilized DBC1 and non-absorbed SIRT1, the non-immobilized component is added to the well containing the immobilized protein under conditions that are conducive to complexation. After the reaction is complete, unbound components are removed by washing and the compound being tested for its ability to disrupt the interaction between SIRT1 and DBC1 is added to the microtiter wells containing the complexed SIRT1 and DBC1. Control reaction mixtures are incubated in the absence of the compound being tested. After the reaction is complete, the plates are washed to remove any unbound protein. The detection of immobilized SIRT1 or immobilized DBC1 can be performed using an indirect label, e.g. using a labeled antibody specific for the immobilized component (the antibody can be directly labeled or indirectly labeled with, for example, a labeled anti-IgG antibody).

Alternatively, this assay can be used to determine if a compound can prevent the interaction between SIRT1 and DBC1. Prior to addition of the non-absorbed component to the microtiter well containing the immobilized component, the non-absorbed component is incubated, in a tube, with the compound being tested for its ability to prevent the complexation between SIRT1 and DBC1. Control reaction mixtures are incubated in the absence of the compound being tested. The treated non-absorbed component is added to the well containing the immobilized component and incubated under conditions conducive to complex formation. After the reaction is complete, the microtiter plate is washed to remove any unbound components. Detection of the immobilized component is performed as described above.

Determining the increase in unbound SIRT1 or the decrease in the complexation of SIRT1 and DBC1 can be performed using surface plasmon resonance, also referred to as light scattering or Biomolecular Interaction Analysis (BIA) (Huber, W. and Mueller, F. (2006) *Curr Pharm Des.* 12(31):3999-4021). "Surface plasmon resonance" detects biospecific interactions in real time, without labeling any of the components. Changes in the mass at the binding surface (indicative of a binding event or the disruption of a binding event) result in changes in the refractive index of light near the surface resulting in a detectable signal which can be used to determine interactions between biological molecules.

Fluorescence based assays can also be used to evaluate the binding of one molecule to another. Fluorescence energy transfer (FET or FRET for fluorescence resonance energy transfer)(see Lakowicz et al., U.S. Pat. No. 5,631,169; Stavrianopoulos, et al., U.S. Pat. No. 4,868,103) requires at least one molecule to be fluorescently labeled. The fluorophore on one molecule, the 'donor' molecule, is selected so that its emitted fluorescent energy will be absorbed by a fluorescent label on a second molecule, the 'acceptor' molecule, which can now emit fluorescence due to the absorbed energy. Changes in the levels fluorescence upon addition of an agent being tested for its ability to disrupt or inhibit the complexation between DBC1 and SRT1 can be measured using standard fluorometric detection means.

To determine the increase in SIRT1 assay an in vitro tubulin deacetylation assay (North, 2003) can be used wherein cellular lysates which contain endogenous SIRT1 and DBC1 are incubated with the agent being tested for its ability to disrupt or inhibit the complexation between SIRT1 and DBC1 followed by Western blotting of these lysates with antisera specific for acetylated α-tubulin and for total α-tubulin.

The yeast two-hybrid system can use SIRT1 as 'bait' and DBC1 as 'prey' to evaluate disruption of the complexation between SIRT1 and DBC1 (see Fields, S, and Sternglanz, R. (1994) *Trends Genet.* 10(8):286-92; and Lambertson, et al., U.S. Pat. No. 6,562,576). The two hybrid system utilizes separable DNA-binding and activation domains in two different DNA construct. Briefly, in one construct, the gene for the SIRT1 protein or the portion of the SIRT1 gene encoding the DBC1 binding domain peptide is fused to a gene encoding the DNA binding domain of a known transcription factor (e.g. GAL-4). The gene for the DBC1 protein of the portion of the DBC1 gene encoding the SIRT1 binding domain peptide is fused to a gene that codes for the activation domain of a known transcription factor. When the complexation forms between DBC1 and SIRT1 or their respective binding domain, the DNA-binding domain and the activation domain of the transcription factor are brought in close proximity allowing transcription of a reporter gene (e.g., LacZ). Conducting the two hybrid assay in the presence of an agent being tested for its ability to modulate the complexation of DBC1 and SIRT1 can determine if it increases or decrease the binding between DBC1 and SIRT1.

Cell Based Assays

A deacetylation assay using p53 protein or a histone as the deacetylation target can be used to determine if the activity of SIRT1 is increased or decreased as a result of modulating DBC1 activity. Briefly, a cultured mammalian cell line is treated with the agent being tested for its ability to modulate DBC1 activity or expression and the level of deacetylation of the target is determined by western blotting. A higher level of acetylation of the target in the treated cells relative to the control indicates that DBC1 activity or expression has decreased. A lower level of acetylation of target in the treated cells as compared to the control indicates that DBC1 activity or expression has increased.

Another useful assay is the adipogenesis assay (for example, see Nayagam, V. M., et al., (2006) *Journal of Biomolecular Screening* 11(8):959-967). The process of adipogenesis can be reconstituted using NIH3T3L1 mouse fibroblasts. Treatment of the cell line with a combination cocktail consisting of dexamethason, isobuytlmethylxanthine (IBMX) and insulin stimulate differentiation of the cells into mature adipocytes, where the cell can produce lipid droplets, which can be stained with Red Oil O and visualized microscopically. Reduction in lipids after treatment with an agent indicates fat mobilization.

EXAMPLES

Example 1

SIRT1 Interacts with DBC1

To understand the regulation of SIRT1-mediated deacetylation in vivo, biochemical purification was used to identify cellular factors that stably interact with SIRT1 under native conditions. Physiologically-formed protein complexes containing SIRT1 from cell extracts of native HeLa cells by conducting affinity chromatography with either a control antibody column or a column coupled to affinity-purified antisera raised against the C-terminus (aa. 480-737) of SIRT1 were isolated. The eluted proteins were then fractionated by SDS-PAGE and visualized by colloidal-blue staining (FIG. 1a). SIRT1 was identified as the major component of the complexes but several protein bands were also co-purified with SIRT1. Previously studies have identified 14-3-3 as a binding partner for SIRT1 (ref. 20). To validate the affinity-purified SIRT1 complexes, 14-3-3σ was identified from the complexes (FIG. 1b). Mass spectrometric analysis of a prominent ~140 kDa protein band from the SIRT1 complexes revealed peptide sequences corresponding to the DBC1 protein (GeneBank accession number Gi:24432106). The DBC1 (Deleted in Breast Cancer 1) gene was initially identified as it is localized to a region of chromosome 8p21 that was homozygously-deleted in human breast cancer; however, the molecular function of DBC1 is poorly understood (Hamaguchi, 2002). Its N-terminal sequences contain a leucine zipper and a nuclear localization signal (NLS), and the C-terminal sequences harbor an EF hand (calmodulin-like calcium-binding region) and a coiled-coil domain (FIG. 1c) and a potential role of DBC1 in apoptosis was implicated (Sundararajan, 2005).

Figure 2:
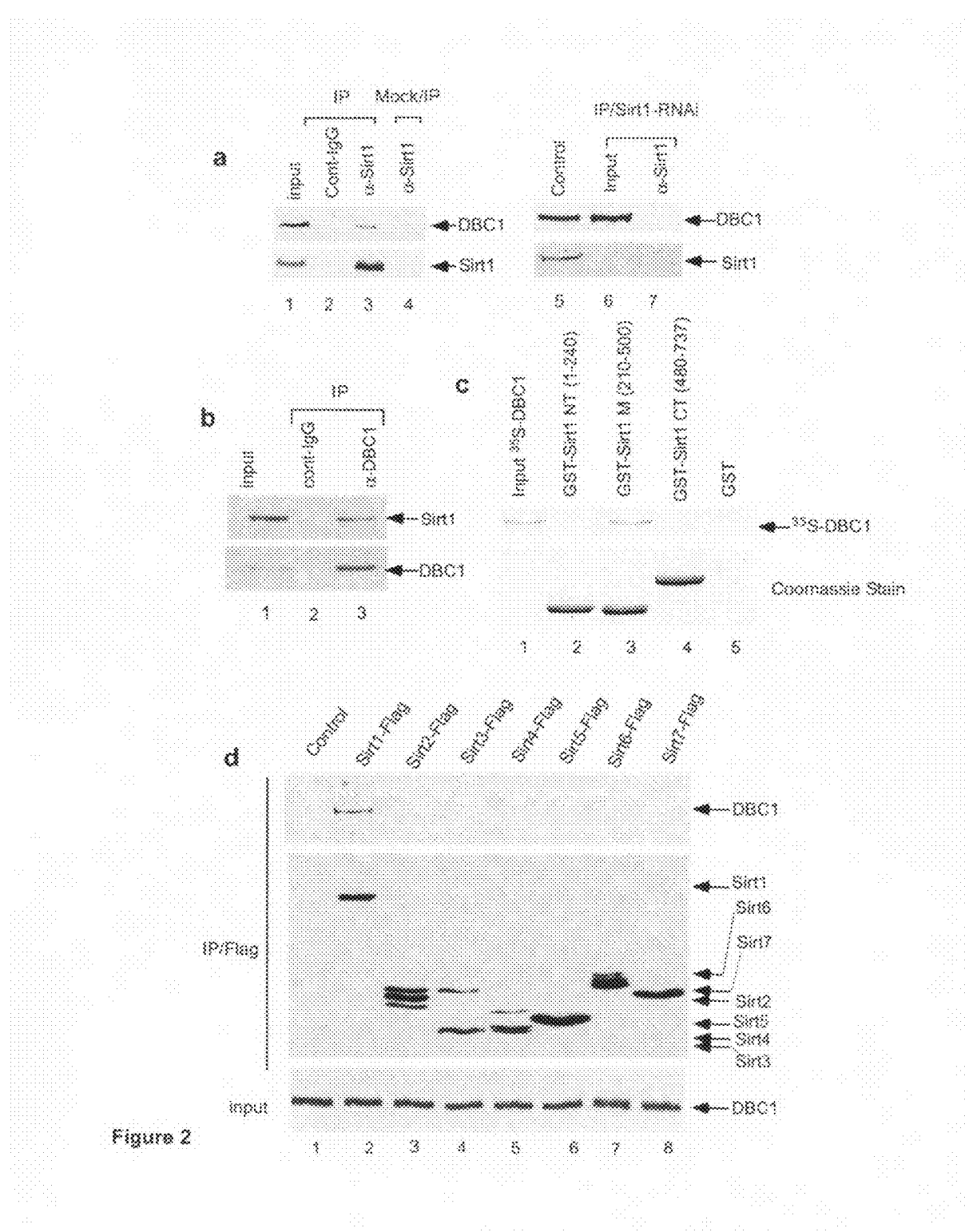
FIG. 2. Characterization of the interaction of DBC1 and SIRT1 in vivo and in vitro. (a) Coimmunoprecipitation of DBC1 with SIRT1 from U2OS cells. Western Blot analysis (left panel) of indicated whole cell extracts (input: lane 1) and immunoprecipitates with SIRT1-specific antibody (lane 3), control IgG (lane 2) or mock IP with SIRT1AB (lane 4), by anti DBC1 antibody (upper panel) and anti SIRT1-antibody (lower panel). To confirm the specificity of the interaction, co-immunoprecipitation of DBC1 by SIRT1 (lane 5) was compared to immunoprecipitation performed in cells were SIRT1 was knocked down by SIRT1 RNAi (input: lane 6, IP: Lane 7). (b) Coimmunoprecipitation of endogenous SIRT1 by DBC1 from U2OS cells. Western blot analysis of indicated whole cell extract (input: lane 1) and immunoprecipitates with DBC1 specific antibody (lane 3) or control IgG (lane 2) with SIRT1 antibody (upper panel) or DBC1 antibody (lower panel). (c) Direct interaction of DBC1 with GST-SIRT1. The N-terminus of SIRT1 (lane 2), the core-domain (lane 3), the C-terminus (lane 4), or GST alone (lane 5) were used in a GST pull-down assay with in vitro translated $^{35}$S-labelled DBC1. $^{35}$S-DBC1 was detected by autoradiography (upper panel) and the GST-fragments were visualized after pull-down by Coomassie Staining (lower panel). (d) DBC1 interacts specifically with SIRT1, but none of the other SIRT family members in vivo. 293 cells were transfected with expression vectors encoding Flag-tagged SIRT family members (lanes 2-8) as indicated. The cell extracts (bottom panel) and M2-immunoprecipitates (upper panels) were analyzed by Western Blot using anti-DBC1 and anti-FLAG antibody (M2) as indicated.
Figure 6:
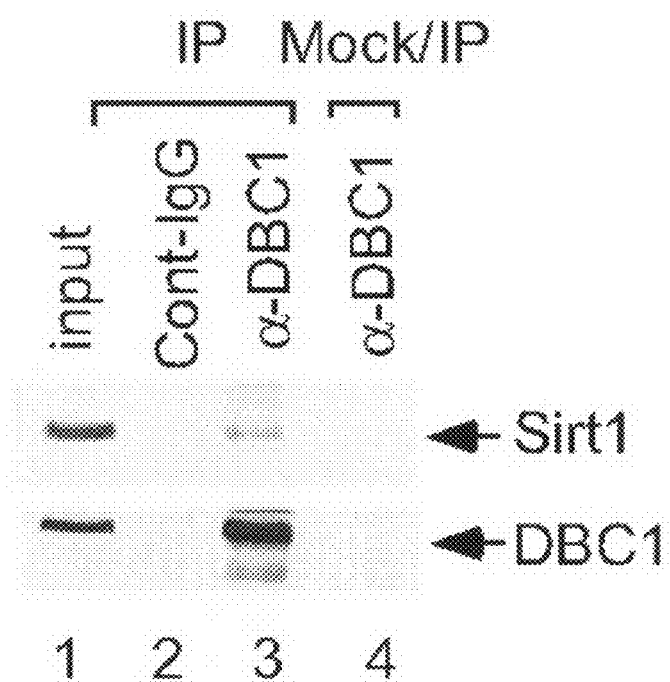
FIG. 6. Endogenous SIRT1 is coimmunoprecipitated by DBC1. Coimmunoprecipitation of SIRT1 with DBC1 from U2OS cells. Western Blot analysis of whole-cell extract (input, lane 1) and immunoprecipitates with a DBC1-specific antibody (lane 3) or control IgG (lane 2) or mock IP with DBC1 antibody alone (lane 4) by anti DBC1 antibody (lower panel) and SIRT1 (upper panel).

To examine the interaction between endogenous DBC1 and SIRT1, cell extracts from human osteosarcoma U2OS cells were immunoprecipitated with the α-SIRT1 antibody or with the control IgG. Western blot analysis revealed that DBC1 was clearly detected in the immunoprecipitations obtained with the α-SIRT1 antiserum (lane 3, FIG. 2a) but not with the control antibody (lane 2). To prove the specificity of the SIRT1 antibody, the co-immunoprecipitation in SIRT1-depleted U2OS cells treated with SIRT1-specific RNAi (lanes 6, 7) was performed. DBC1 was not detected in the α-SIRT1 immunoprecipitates with these SIRT1-depleted cells (lane 7). A reciprocal co-immunoprecipitation assay was performed also. As shown in FIG. 2b, endogenous SIRT1 was readily immunoprecipitated with the DBC1-specific antibody (lane 3), but not with a control antibody (lane 2). Moreover, to further support the specificity of these interactions, mock immunoprecipitations of either DBC1- or SIRT1-specific antibodies with no cell extract as negative controls were included (lane 4, FIG. 2a; lane 4, FIG. 6).

Figure 7:
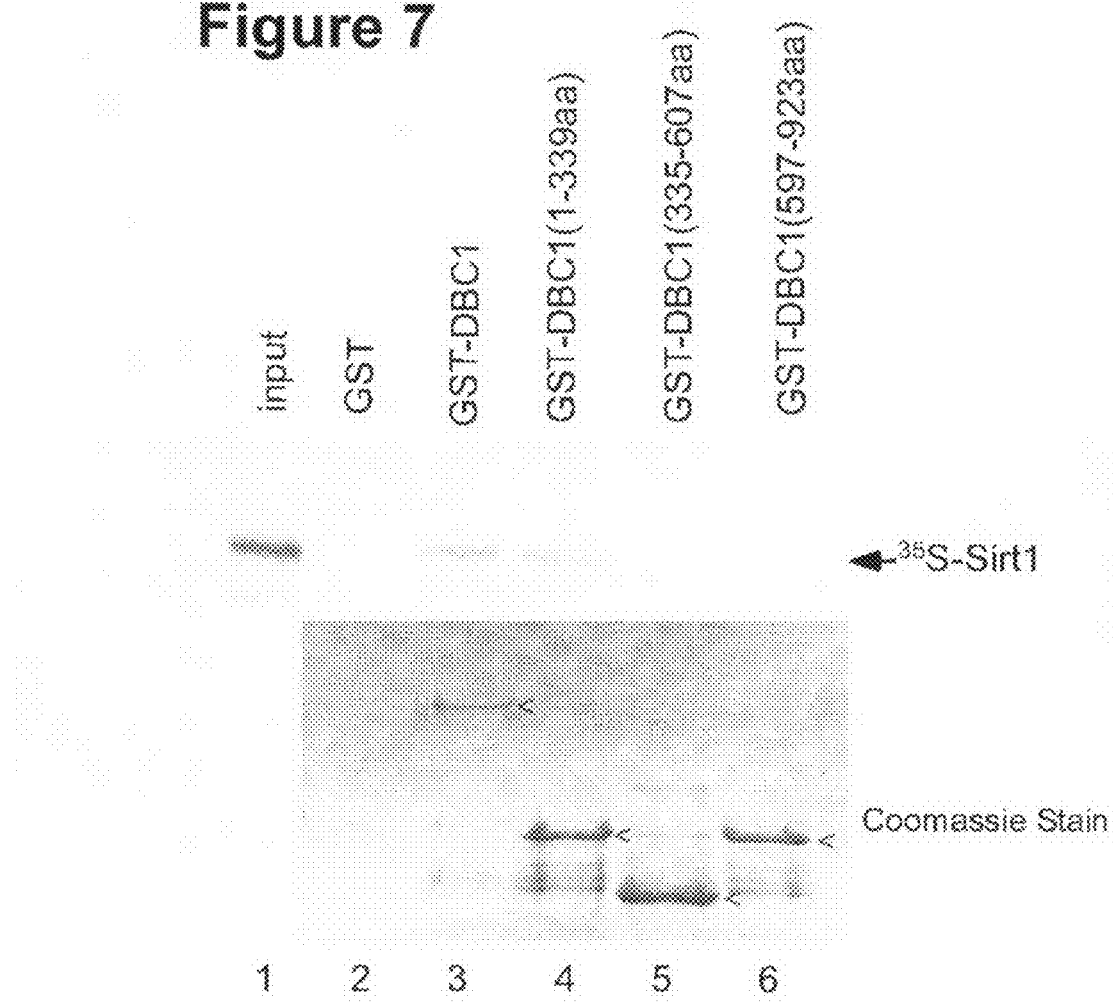
FIG. 7. SIRT1 interacts with DBC1 in vitro. Full-length DBC1 (lane 3) as well as GST-NT-DBC1 (lane 4), GST-M-DBC1 (lane 5), GST-CT-DBC1 (lane 6) and GST alone were used in a GST pull-down assay with in vitro translated $^{35}$S-labelled SIRT1. $^{35}$S-SIRT1 was detected by autoradiography (upper panel), while the GST-proteins were detected by Coomassie-Stain (lower panel).
Figure 8:
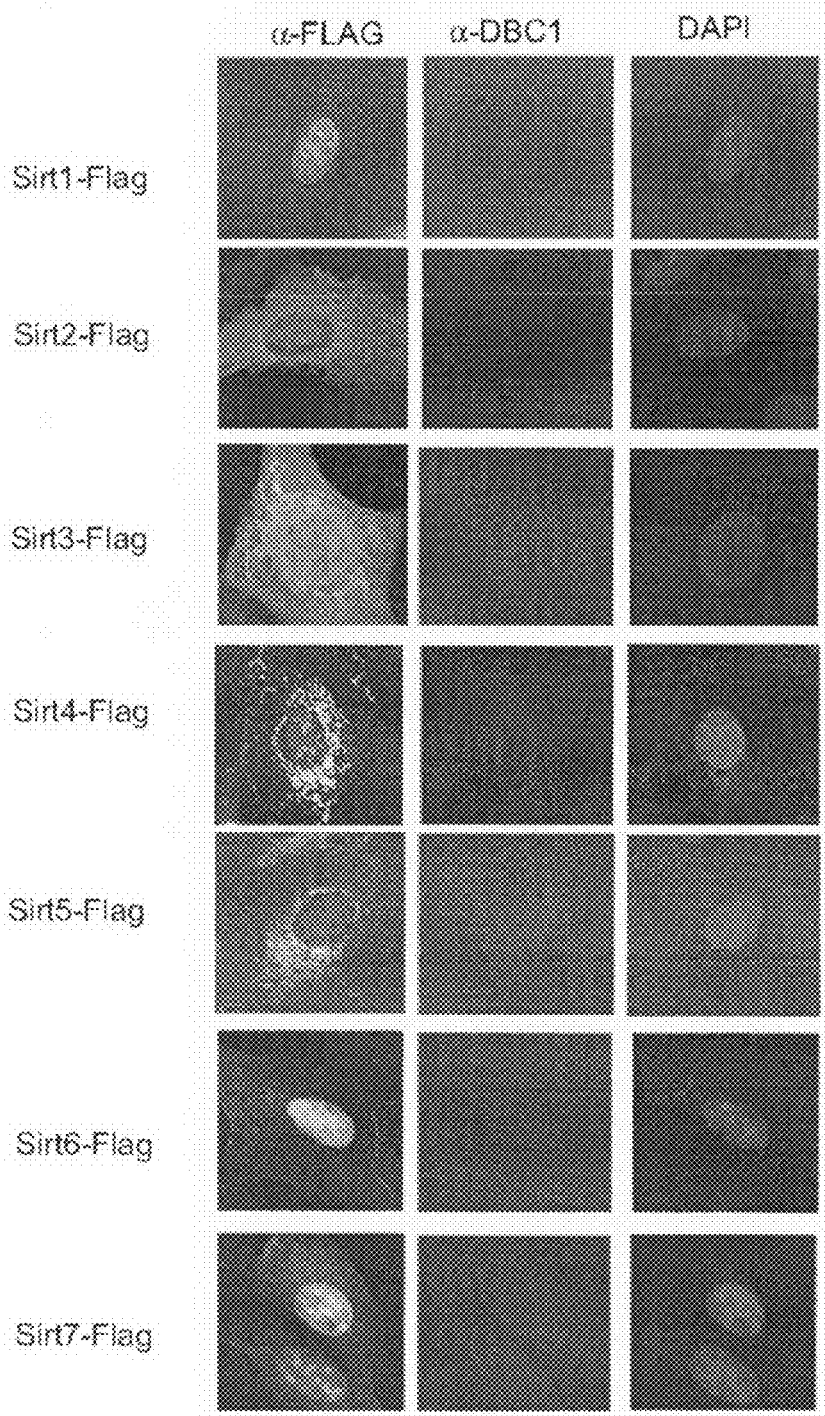
FIG. 8. Sub-cellular localization of SIRT family members and DBC1. U2OS cells were transfected with Flag-tagged expression constructs of the SIRT family members as indicated. To investigate the sub-cellular localization of the different SIRT family members, cells were co-stained using FLAG antibody for the exogenous SIRT protein and DBC1 antibody for endogenous DBC1.

Next, whether SIRT1 binds DBC1 in vitro was tested. As shown in FIG. 2c, $^{35}$S-labeled in vitro-translated DBC1 bound the central core domain of SIRT1 (GST-SIRT1-M) (lane 3) but showed no affinity for either its N-terminal (GST-SIRT1-NT) (lane 2) or C-terminal (GST-SIRT1-CT) (lane 4) domains, although comparable amounts of each GST-fusion protein was tested. The N-terminus of DBC1 as the SIRT1 binding domain was identified (FIG. 7). Since the enzymatic core sequence represents the most conserved region of mammalian SIRT protein family, whether DBC1 interacts with other members of this family was determined. Flag-tagged derivatives of the seven human SIRT polypeptides (SIRT1-7) were each expressed in 293 cells and extracts of the transfected cells were immunoprecipitated with the α-Flag antibody. Western blot analysis revealed that endogenous DBC1 was clearly detected in the immunoprecipitates of Flag-SIRT1 (lane 2, FIG. 2d). Although similar expression levels for all seven Flag-SIRT polypeptides were detected, none of the other SIRT proteins (SIRT2, SIRT3, SIRT4, SIRT5, SIRT6 and SIRT7) were able to co-immunoprecipitate DBC1 (lanes 3-8, FIG. 2d). These results demonstrate the specificity of the SIRT1 and DBC1 interaction.

Example 2

DBC1 Inhibits SIRT1 Deacetylase Activity

Figure 3:
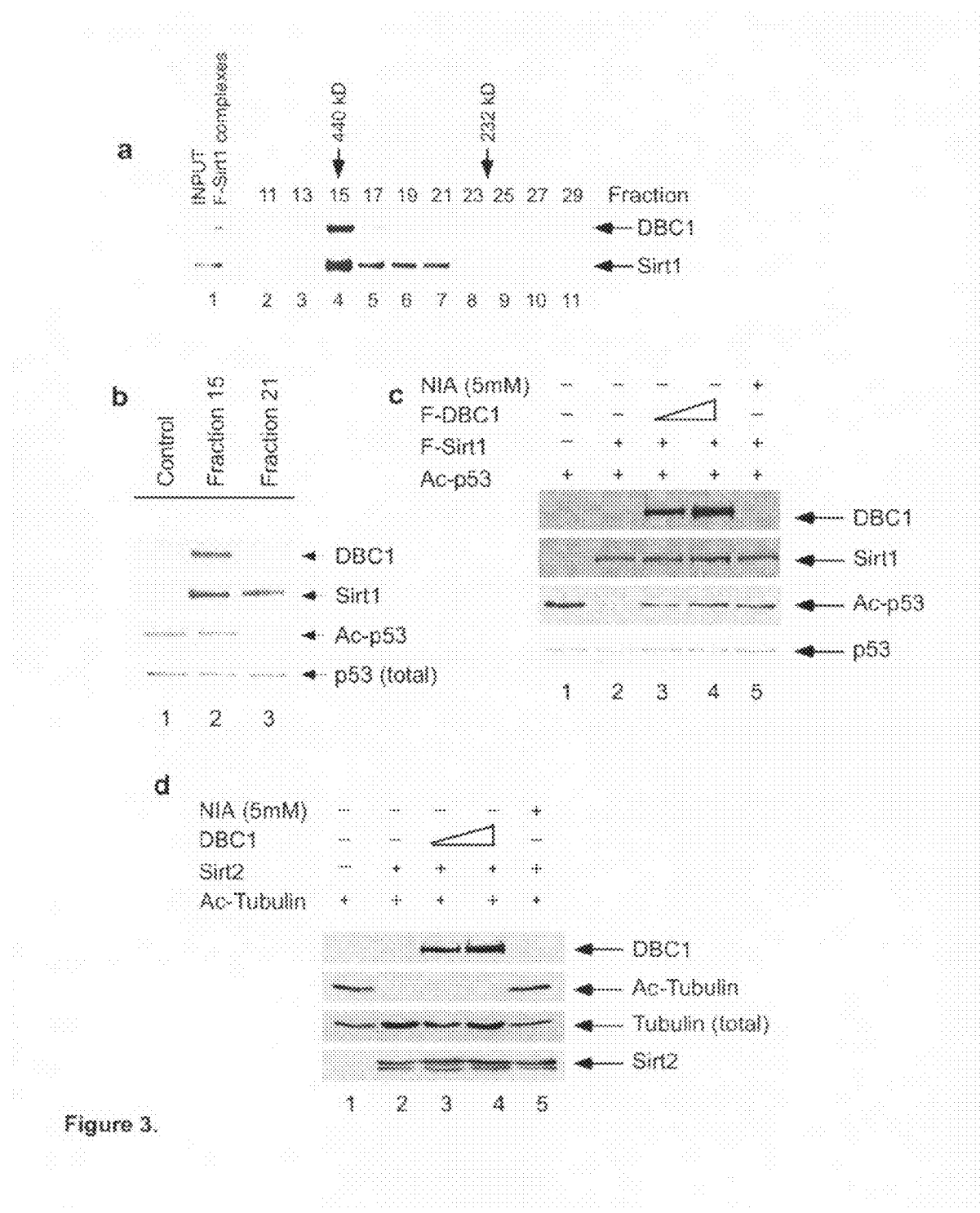
FIG. 3. DBC1 inhibits SIRT1 mediated deacetylation of p53 (a) Fractionation of immunoprecipitated F-SIRT1 complex. 293 cells were transfected with Flag-tagged SIRT1 and Flag-SIRT1 complexes were subsequently purified by M2-immunoprecipitation in FLAG-lysis buffer. Flag-SIRT1 complex was eluted in 100 ul of elution buffer and half of the elution was fractioned by size-exclusion chromatography on a Sepherose12 Column on the SMART system. 10% of each fraction was analyzed by Western Blot for DBC1 (upper panel) and SIRT1 (lower panel). (b) DBC1 inhibits SIRT1 mediated deacetylation of p53 in vitro. The enzymatic activity of F-SIRT1 complex fractions (generated using the SMART system described in FIG. 3a) with of without DBC1 (Fraction 15, lane 2; and Fraction 21, lane 3 respectively) was tested by an in vitro deacetylation assay using acetylated p53 as a substrate. The reactions were resolved on SDS-PAGE and analyzed by Western Blot using antibodies specific for acetylated p53, total p53 (DO-1), SIRT1 and DBC1. (c) DBC1 inhibits SIRT1 mediated deacetylation of acetylated p53 in a dose dependent manner in vitro. F-SIRT1 and F-DBC1 were purified by M2 immunoprecipitation under high stringency (500 mM NaCl, 0.5% Triton-X) and used in in vitro deacetylation assays with acetylated p53 as a substrate. Increasing amounts of pure F-DBC1 (lanes 3, 4) or the known SIRT1 inhibitor Nicotinamide [5 mM] (lane 5) were added to the reaction to inhibit the SIRT1 mediated deacetylation (lane 2). The reactions were resolved on SDS-Page and analyzed by Western Blot using antibodies specific for acetylated p53, total p53, SIRT1 and DBC1. (d) DBC1 does not inhibit SIRT2 mediated deacetylation of acetylated tubulin in vitro. F-SIRT2 and F-DBC1 were purified by M2 immunoprecipitation under high stringency (500 mM NaCl, 0.5% Triton-X) and used in in vitro deacetylation assays with acetylated tubulin as a substrate. Increasing amounts of pure F-DBC1 (lanes 3, 4) or the known SIRT2 inhibitor Nicotinamide [5 mM] (lane 5) were added to the reaction to inhibit the deacetylation reaction (lane 2).

Although the deacetylase activity of SIRT1 is essential for its function, it is unknown how this activity is regulated. When purified Flag-SIRT1 complexes from human cells were analyzed by gel-filtration chromatography on a Superose 12 column (SMART system), SIRT1 and DBC1 polypeptides co-eluted in fraction 15 with an apparent molecular weight of 440 KDa (lane 4, FIG. 3a). In contrast, the DBC1-free form of SIRT1 eluted in fractions 19 to 21 (lanes 6, 7), suggesting that at least two distinct SIRT1 complexes exist in human cells. SIRT1 from fraction 21 had a strong NAD-dependent deacetylase activity for p53 (lane 3, FIG. 3b). No activity was detected with fraction 15 (lane 2), raising the notion that SIRT1-mediated deacetylation is inhibited by additional factors in the complexes, such as DBC1. To evaluate a role for DBC1 in regulating SIRT1 function, whether DBC1 can inhibit the deacetylase activity of SIRT1 in a purified system was examined. Flag-tagged forms of SIRT1 and DBC1 were purified under high stringency conditions for in vitro deacetylation assays. As indicated in FIG. 3c, deacetylation of p53 was observed when the Flag-SIRT1 protein was incubated with acetylated p53 (lane 2). However, this activity was strongly repressed by Flag-DBC1 in a dose dependent manner (lanes 3, 4). DBC-mediated repression is apparently as potent as the effects obtained with 5 mM of nicotinamide (NIA) (lane 5), a known inhibitor of SIRT1-mediated deacetylation (Luo, 2001).

Figure 9:
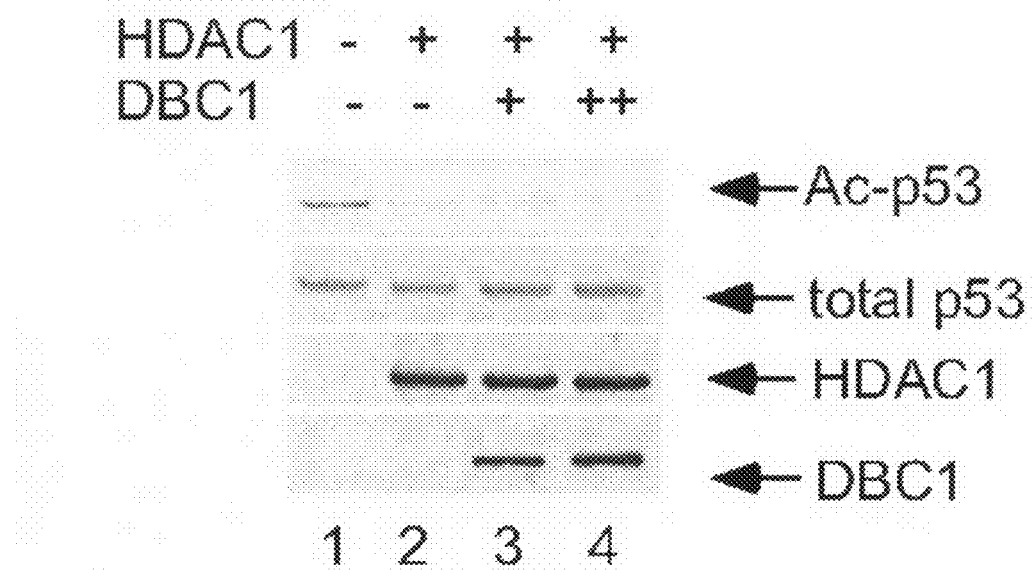
FIG. 9. Effect of DBC1 on HDAC1 mediated p53 deacetylation in vitro. Purified HDAC1 complex was used to deacetylate p53 in vitro (lane 2). Increasing amounts of DBC1 were added in addition to HADC1 (lanes 3-4) to investigate whether DBC1 can inhibit p53 deacetylation by HDAC1. Prior to harvesting, the cells were treated with TSA (10 μM) for 6 hours. The samples were resolved by SDS-PAGE and analyzed by Western Blot using antibodies for acetylated p53, total p53 (DO-1), HDAC1 and DBC1.
Figure 10:
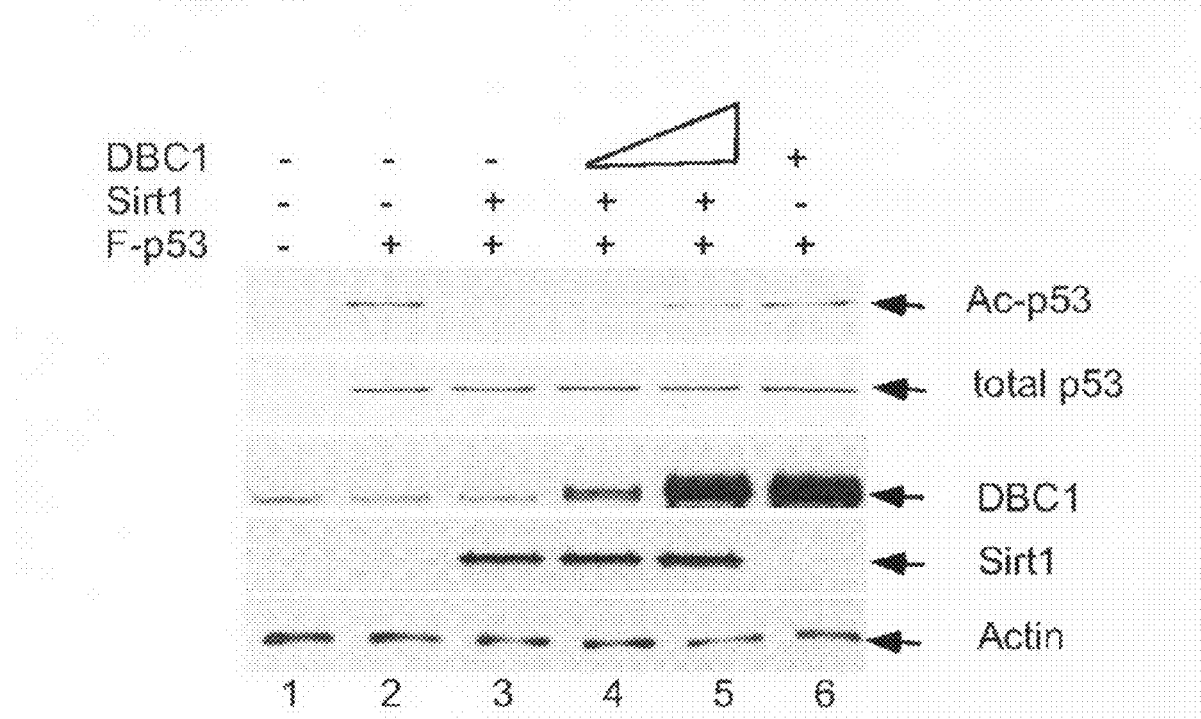
FIG. 10. DBC1 inhibits deacetylation of p53 in vivo. H1299 cells were transfected with expression vectors for Flag-p53, SIRT1 and DBC1 as indicated. Flag-p53 was immunoprecipitated and whole cell lysates (lower four panels) and immunoprecipitates (top panel) were resolved by SDS-PAGE and analyzed by Western Blot using antibodies as indicated.
Figure 11:
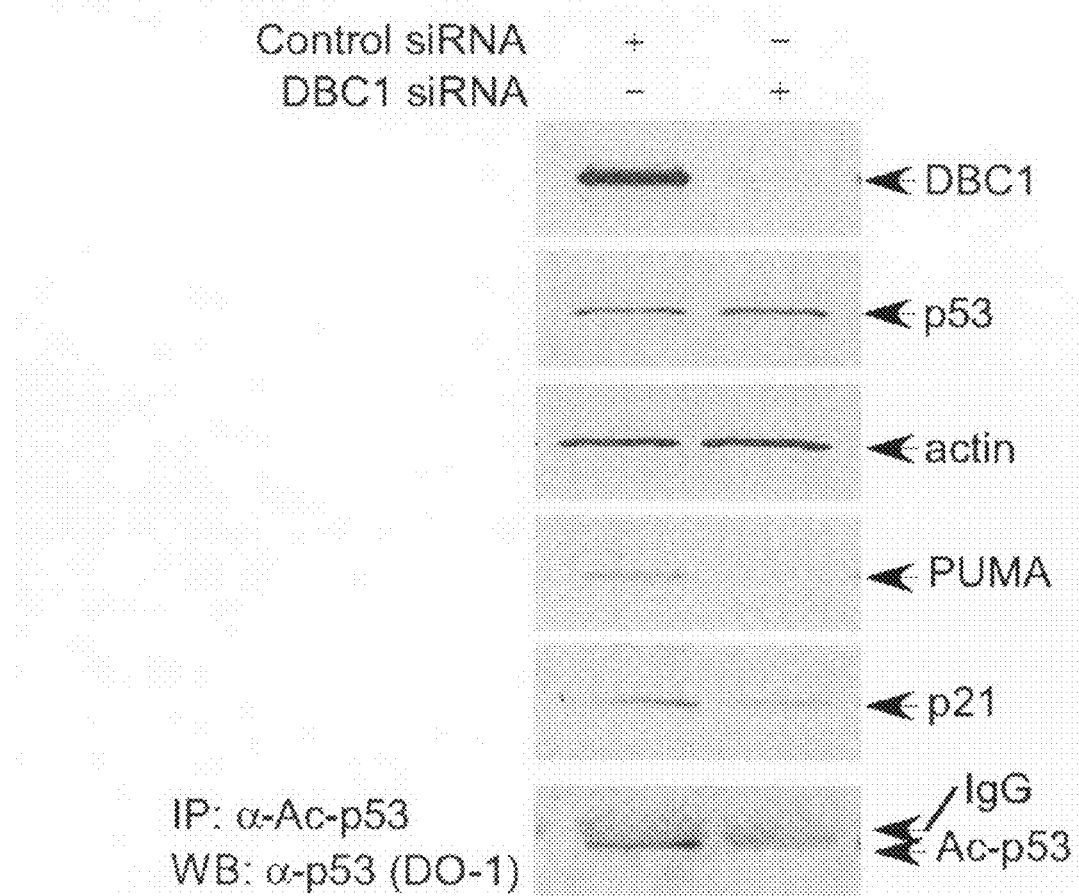
FIG. 11. siRNA-mediated ablation of the endogenous DBC1 protein. Western Blot analysis of the whole cell extracts of U2OS cells treated with either DBC1 siRNA or control siRNA using antibodies against DBC1, p53 (DO-1), PUMA, p21, and actin (upper 5 panels). Western blot analysis of the immunoprecipitates by anti-acetylated p53 antibody and normal IgG from U2OS cells using anti-p53 (DO-1) antibody (lower panel).
Figure 12:
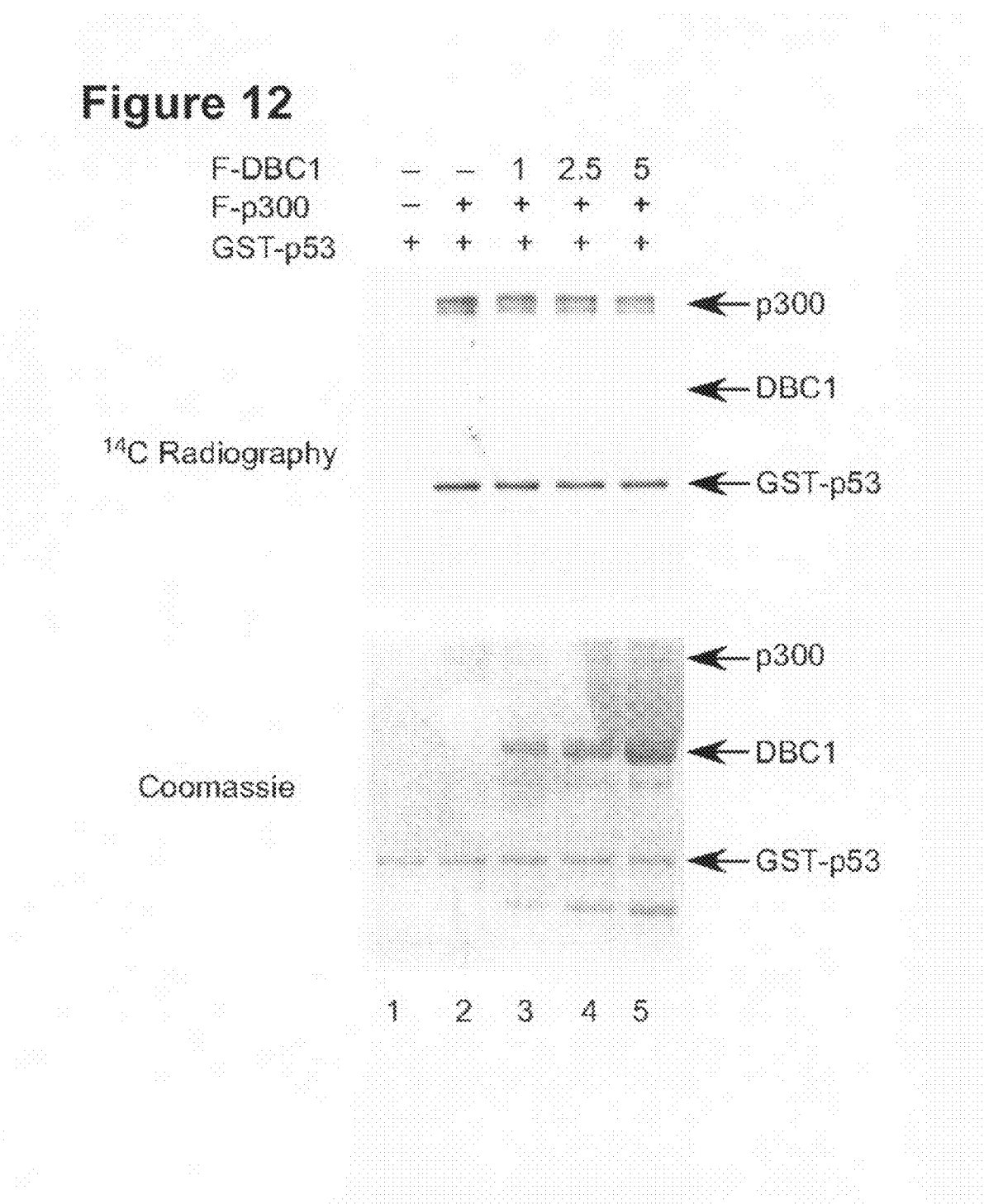
FIG. 12. Effect of DBC1 on p300 mediated p53 acetylation in vitro. Purified GST-p53 was used as a substrate for acetylation by p300 in vitro (lane 2). Increasing amounts of purified DBC1 were added (lanes 3-5) to the reactions. The reactions were resolved by SDS-PAGE and acetylated GST-p53 and self-acetylated F-p300 were visualized by autoradiation (labeling by $^{14}C$-labeled Ac-CoA) (upper panel). All protein levels were visualized by Coomassie Staining (lower panel).
Figure 13:
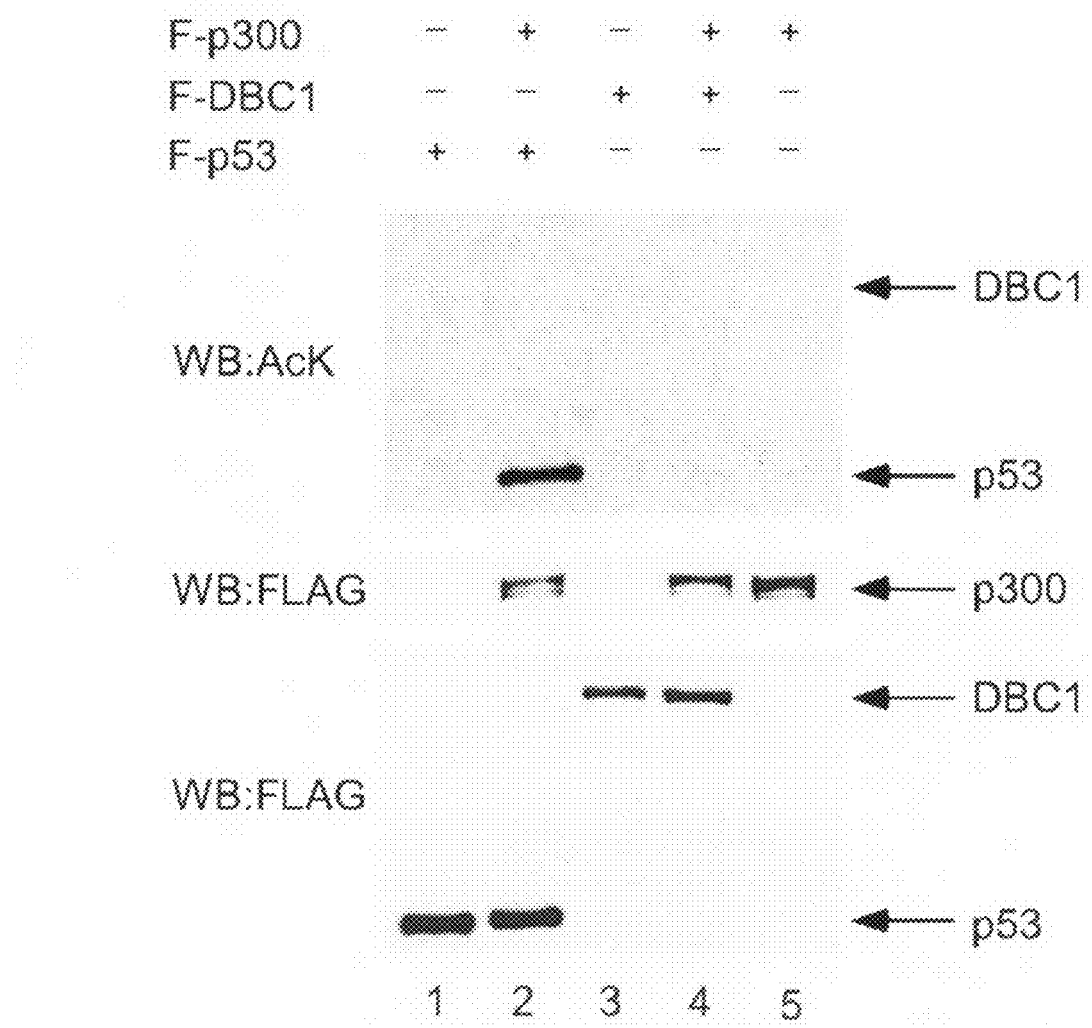
FIG. 13. p300 mediated acetylation of p53 and DBC1 in vivo. H1299 cells were transfected with expression vectors for either Flag-p53 or F-DBC1 with or without F-p300 as indicated. Flag-tagged proteins were M2-immunoprecipitated, resolved by SDS-PAGE and analyzed by Western Blot using an acetylated-Lysine antibody (upper panel), or Flag Antibody (middle and lower panel).
Figure 14:
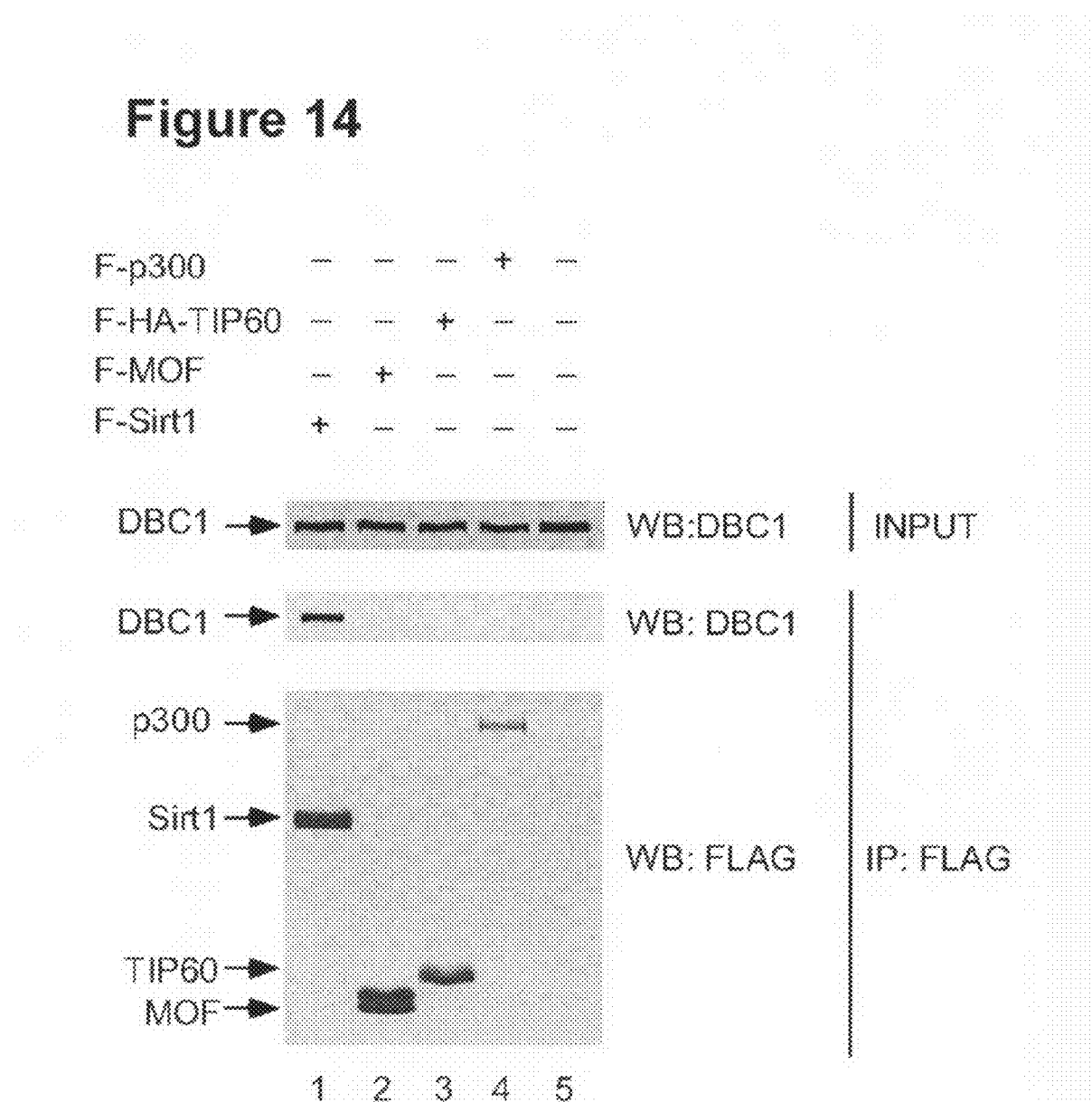
FIG. 14. Interaction of DBC1 with SIRT1 or HATs in vivo. H1299 cells were transfected with expression vectors for Flag-SIRT1 (lane1), Flag-MOF (lane 2), Flag-HA-TIP60 (lane 3) and Flag-p300 (lane 4) and control vector (lane 5). The tagged proteins were M2-immunoprecipitated and inputs and immunoprecipitates were resolved by SDS-PAGE and analyzed by Western Blot using DBC1 specific antibody for the input (upper panel), DBC1 after immunoprecipitation (middle panel) and Flag-Antibody (bottom panel).
Figure 15:
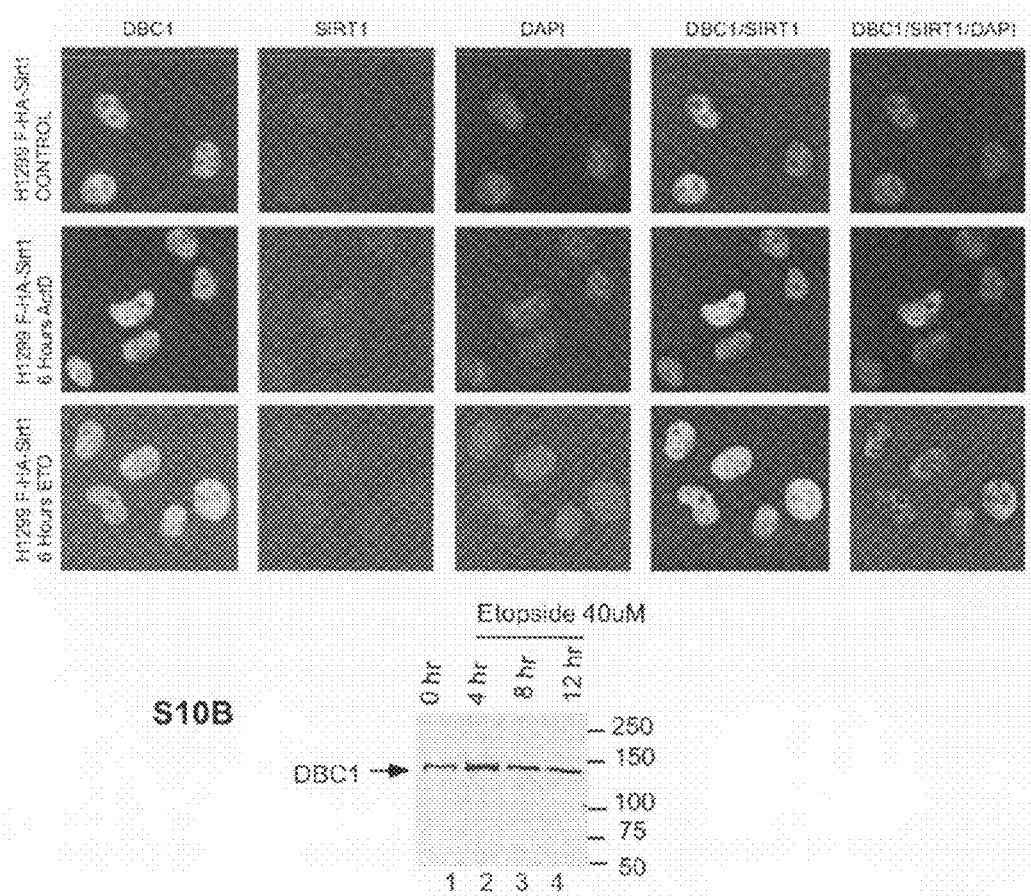
FIG. 15. Effect of DNA-Damage on sub-cellular localization of SIRT1 and DBC1. (S10A) The localization of DBC1 is not regulated upon DNA damage. A stable cell line of H1299 cells expressing F-HA-SIRT1 was used to analyze the sub-cellular localization of endogenous DBC1 and SIRT1 either untreated (upper row) or after treatment with either Actinomycin D (middle Panel) or Etoposide (lower Panel) for 6 hours. In all cases DBC1 and SIRT1 co-localize to the nucleus and are not affected by the treatment. (S10B) No truncation forms of DBC1 are induced upon DNA damage. Western blot analysis of endogenous DBC1 from U2OS cells harvested at different time points after treated with Etoposide.
Figure 16:
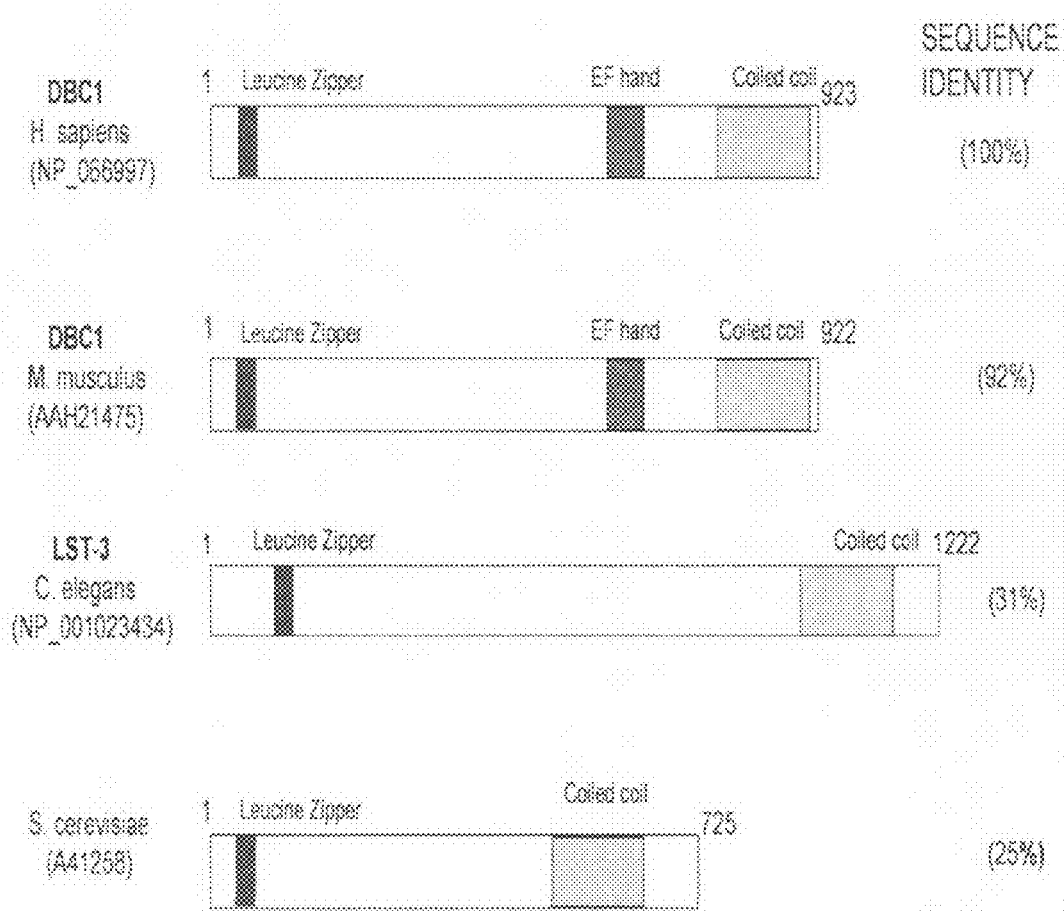
FIG. 16. Schematic Representation of the DBC1 protein family based on bioinformatic analysis.

Moreover, to further prove the specificity of DBC-mediated inhibition of SIRT1 deacetylase activity, the effect of DBC1 on SIRT2-mediated deacetylation of tubulin was examined. As shown in FIG. 3d, deacetylation of tubulin was observed when the purified SIRT2 protein was incubated with acetylated tubulin as previously reported (North, 2003). This activity was also inhibited by nicotinamide (lane 5); however, tubulin deacetylation by SIRT2 was not affected by purified DBC1 polypeptides (lanes 3, 4). Finally, p53 could also be deacetylated by purified HDAC1 complexes as previously shown (Luo, 2000) (lane 2, FIG. 9); this deacetylase activity was not repressed by DBC1 (lanes 3-4). These data demonstrate that DBC1-mediated inhibitory effects specifically act on SIRT1 deacetylase activity.

Figure 4:
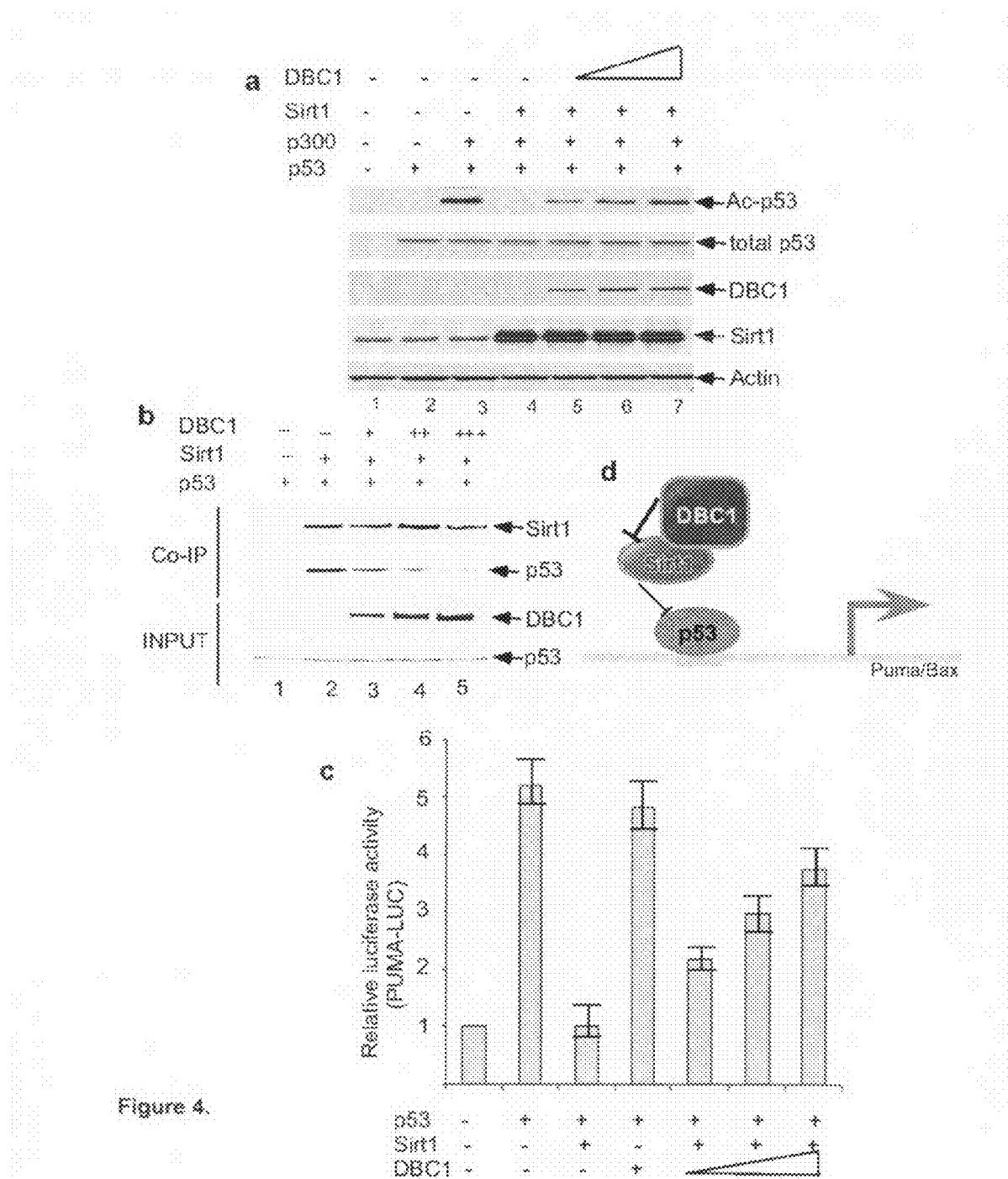
FIG. 4. DBC1 acts as an inhibitor of SIRT1 in human cells. (a) DBC1 represses the deacetylation activity of SIRT1 in vivo. H1299 cells were transfected with expression vectors for p53 and p300 in combination with SIRT1 alone (lane 4) or SIRT1 and increasing amounts of DBC1 (lanes 5-7). The cell extracts were analyzed by Western Blot using antibodies specific for acetylated p53, total p53 (DO-1), SIRT1 and DBC1. (b) DBC1 inhibits SIRT1 mediated coimmunoprecipitation of p53 in vivo. H1299 cells were transfected with expression vectors for p53, Flag-SIRT1 and HA-DBC1. F-SIRT1 was purified by M2-immunoprecipitation and inputs and immunoprecipitates were resolved by SDS-PAGE and analyzed by Western Blot with antibodies as indicated. (c) DBC1 expression rescues the repression of p53-mediated transcriptional activation by SIRT1. H1299 cells were transfected with the Puma-luciferase promoter construct, the expression vector of p53, in combination with SIRT1 alone or SIRT1 and DBC1 as indicated. Cell extracts were assayed for the dual-luciferase activity. The data were obtained from three independent experiments. (d) A model showing that DBC1 acts as an inhibitor of SIRT1 mediated repression of p53.

Whether DBC1 expression rescues p53 from SIRT1-mediated deacetylation in human cells was further tested. Co-expression of SIRT1 induced p53 deacetylation (lane 4); however, the steady-state levels of acetylated p53 were restored by DBC1 expression in a dose-dependent manner (lanes 5-7). To elucidate the mechanism of DBC-mediated effects on SIRT1, a co-immunoprecipitation assay to test whether the interaction between SIRT1 and p53 is regulated by DBC1 was conducted. As shown in FIG. 4b, p53 was co-immunoprecipitated with SIRT1 (lane 2). The p53-SIRT1 interaction was significantly abrogated by DBC1 expression in a dose dependent fashion (lanes 3-5). These results suggest that DBC1 represses SIRT1 activity in human cells and that these effects may act in part, through blocking the interactions between SIRT1 and substrates (p53).

Example 3

DBC1 Upregulates p53 Activity by Inhibiting SIRT1

To further explore the functional consequences of these interactions, whether DBC1 can influence SIRT1-mediated repression of p53 transcriptional activation was tested. As shown in FIG. 4c, SIRT1 strongly suppressed p53-mediated transactivation of the PUMA reporter in a luciferase assay. Again, this SIRT1-mediated suppression was abrogated by DBC1 expression in a dose-dependent manner. These data indicate that DBC1 can enhance p53-dependent transactivation of PUMA by inhibiting SIRT1. Since homozygous deletion of the DBC1 gene was reported in breast cancers (Hamaguchi, 2002; Sundararajan, 2005; Dai, 2000; Kurimoto, 2001; Martinez-Climent, 2001; Swalwell, 2002) inactivation of DBC1 may enhance the deacetylase activity of SIRT1 and thereby lead to inhibition of p53 function (FIG. 4d).

Figure 5:
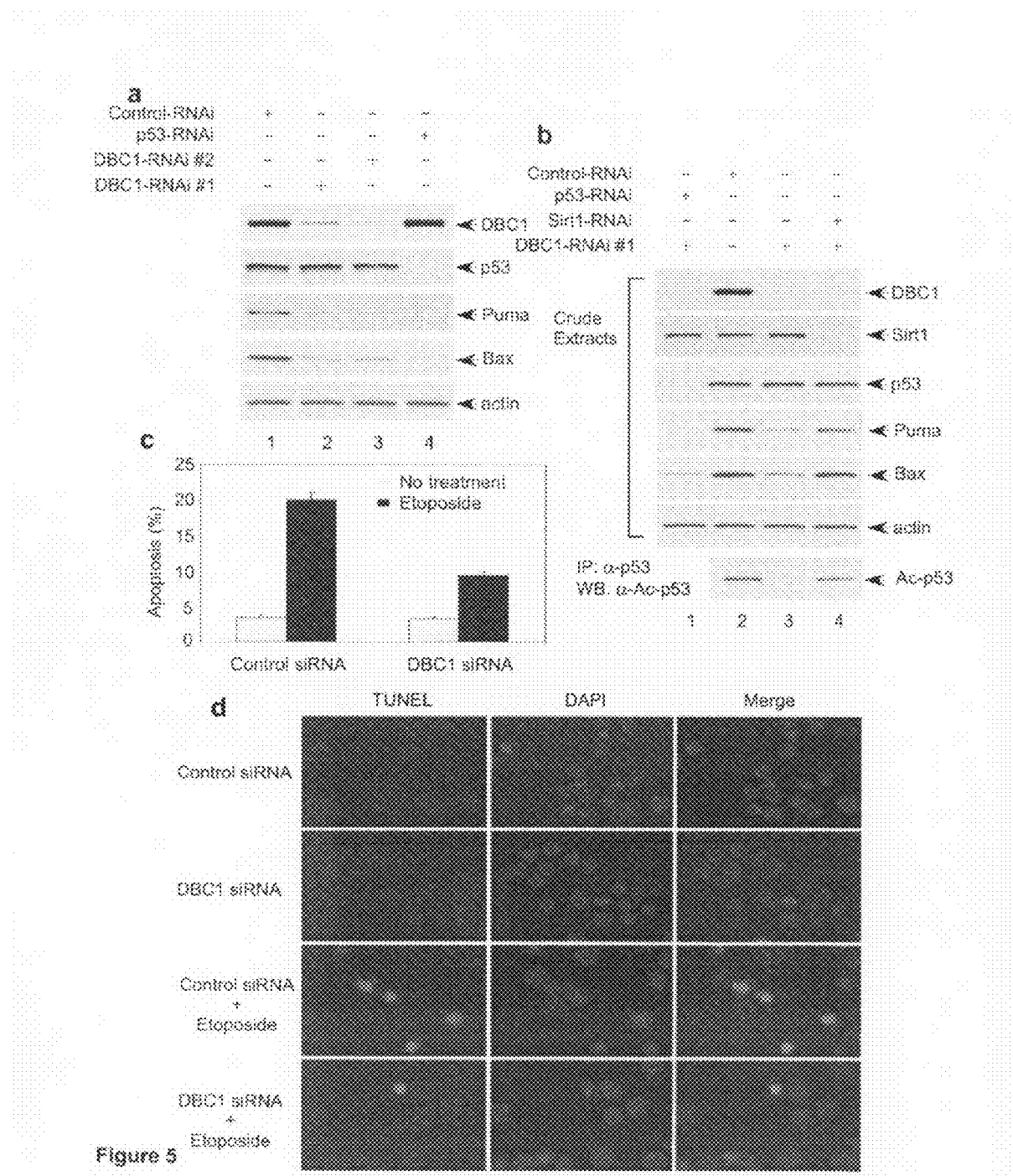
FIG. 5. siRNA-mediated knockdown of DBC1 reduces p53 acetylation and its transcriptional and apoptotic activities. (a) siRNA-mediated ablation of the endogenous DBC1 protein inhibits expression of p53 proapoptotic target genes, Puma and Bax. Western blot analysis of the whole cell extracts from U2OS cells treated with either the control siRNA (lane 1), 2 different DBC1 siRNA (#1: 5'CAGCGGGUCUUCACUG-GUA3' (lane2) (SEQ. ID NO.1); (#2: 5'CAGCUUG-CAUGACUACUUU3' (lane 3) (SEQ ID NO:2) or p53 RNAi (lane 4) using antibodies against DBC1 (BL1924), p53 (DO-1), Puma, Bax, and actin. (b) SIRT1 mediates reduction of p53-dependent Puma and Bax expression by DBC1 siRNA. Western blot analysis of the whole cell extracts from U2OS cells treated with different siRNAs as indicated using antibodies against DBC1 (BL1924), SIRT1, p53 (DO-1), Puma, Bax, and actin (upper panel). The acetylation levels of p53 are shown in the lower panel after p53 was immunoprecipitated. (c, d) In (d), 72 hours after transfection with DBC1 or control siRNA duplexes, U2OS cells were treated with either the control dissolvent DMSO or the DNA damaging reagent Etoposide (20 μM) for 30 hours. The cells were fixed and stained by the TUNEL assay for apoptosis (Green). Nuclei were visualized by DAPI staining (Blue). Apoptosis observed in the TUNEL assay was quantified for three separate experiments and presented as the average mean±standard deviation (SD) (c). (e) U2OS cells were treated with either control siRNA (I), DBC1 siRNA alone (II) or in combination with siRNA for SIRT1 (III) or p53 (IV). After transfection the cells were treated as in indicated and apoptosis was quantitated by annexin V staining followed by FacScan as shown in Fig. S12.
Figure 5:
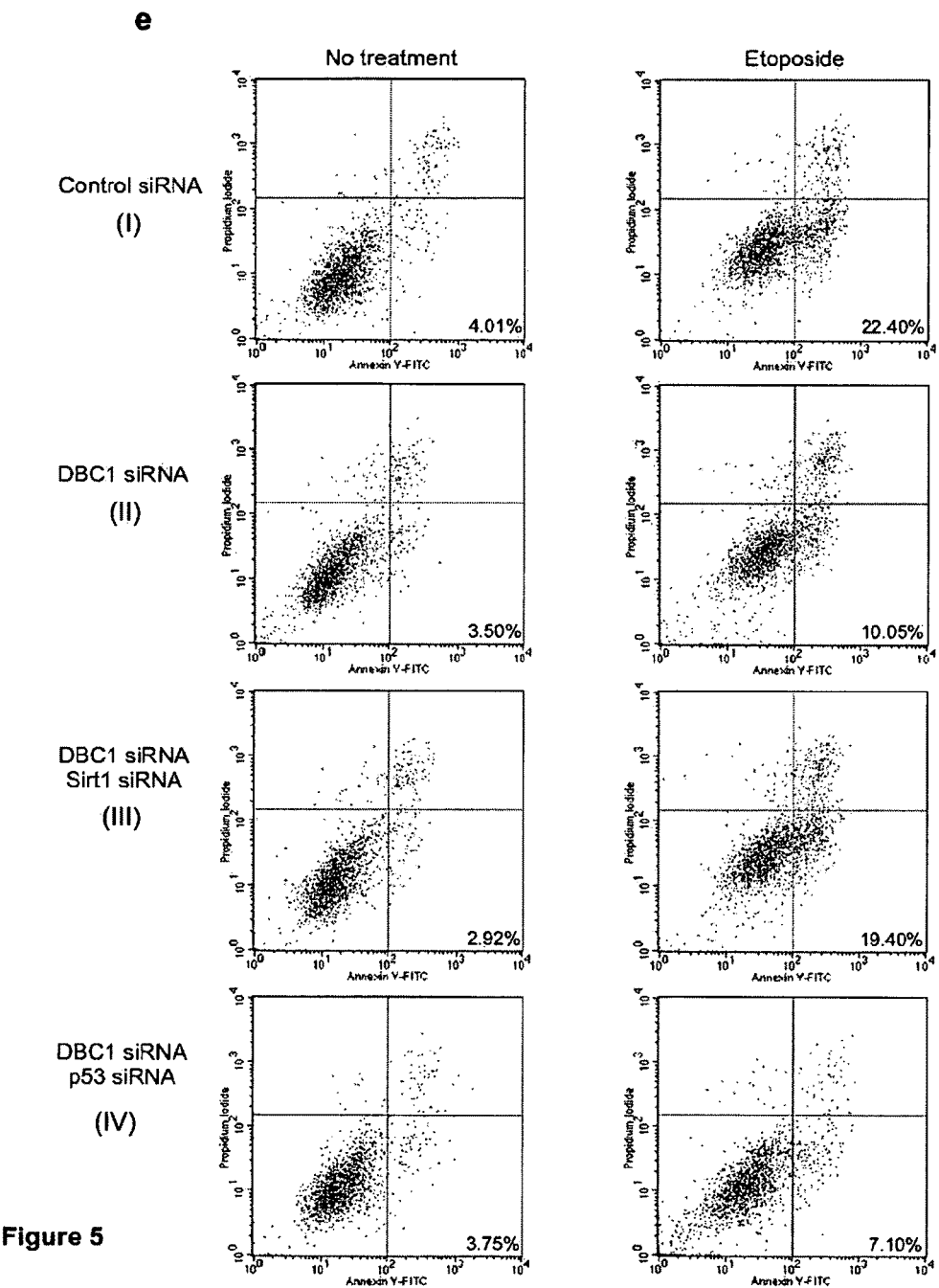

To test the above hypothesis, it was first examined whether siRNA-mediated knockdown of endogenous DBC1 has any effect on p53 function. To avoid possible off-target effects caused by the DBC1 RNAi, two different RNAi sequences that target different regions of the DBC1 mRNA were used. Thus, human osteosarcoma U2OS cells were transfected with the DBC1-specific siRNA#1 (DBC1-RNAi#1), DBC1-specific siRNA#2 (DBC1-RNAi#2), or a control siRNA (Control-RNAi). As shown in FIG. 5a, RNAi-mediated knockdown of DBC1 expression had no obvious effect on p53 stability (lanes 2, 3) but significantly reduced the expression levels of PUMA and Bax, two major transcriptional targets of p53. Knockdown of p53 expression by p53-specific siRNA (p53-RNAi) completely abolished the expression of both PUMA and Bax (lane 4), validating that expression of these two targets is indeed p53-dependent. These experiments demonstrate that inactivation of endogenous DBC1 leads to down-regulation of p53 activity.

Moreover, to demonstrate that DBC1 acts on p53 by repressing SIRT1 deacetylase activity, whether inactivation of DBC1 reduces acetylation levels of endogenous p53 by SIRT1 and more importantly, whether these effects are reversed by inactivation of SIRT1 expression were tested. These cells were transfected with the DBC1-specific siRNA#1 (DBC1-RNAi#1), SIRT1-specific siRNA (SIRT1-RNAi), or a control siRNA (Control-RNAi). As shown in FIG. 5b, RNAi-mediated knockdown of DBC1 expression significantly reduced the acetylation levels of endogenous p53 (Ac-p53, bottom panel, lane 3). Notably, the reduction of p53 acetylation was completely reversed by concomitant knockdown of SIRT1 (Ac-p53, bottom panel, lane 4). Similar results were also observed with DBC1-mediated effects on PUMA and Bax by concomitant knockdown of SIRT1 (PUMA and Bax, middle panel, lane 3, 4). These data demonstrate that DBC1-mediated effects on p53 activation act mainly through SIRT1 in vivo.

Figure 17:
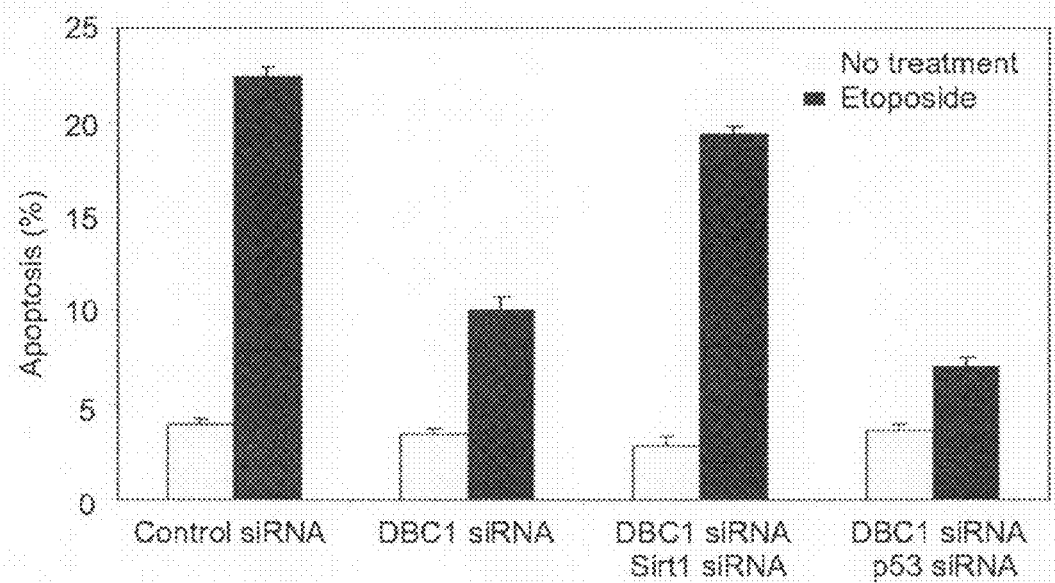
FIG. 17. DBC1 inactivation abrogates p53-mediated apoptosis. Apoptosis observed in the Annexin V assay (FIG. 5e) was quantified and presented as the average mean±standard deviation (SD)

To investigate the role of DBC1 in the stress response, whether inactivation of DBC1 can suppress p53-dependent apoptosis upon DNA damage was tested. For this purpose, U2OS cells were first transfected with either control or DBC-specific siRNAs and then exposed to etoposide. 30 hours later, the cells were stained with DAPI and apoptosis was examined by TUNEL staining. As shown in FIGS. 5c and 5d, the DBC1-depleted cells were highly resistant to apoptosis, displaying only 8.8% apoptotic cells as compared to 20.5% of cells transfected with the control siRNA. To further confirm the role of DBC1 in regulating p53-mediated apoptosis, an apoptosis assay by using Annexin V staining followed by flow-cytometry analysis was performed and again, p53-mediated apoptosis was repressed in DBC1 knockdown cells (II, FIG. 5e, and FIG. 17). Inactivation of p53 in these cells completely abolished the apoptotic response by DNA damage (IV, FIG. 5e, and FIG. 17). Notably, concomitant knockdown of SIRT1 reversed the inhibitory effects on p53-dependent apoptosis by DBC inactivation (III, FIG. 5e, and FIG. 17). These data demonstrate that DBC1 is critically involved in regulating the p53-mediated apoptotic response by repressing SIRT1 function.

Example 4

Materials and Methods for Examples 1-3

Cell Culture and Transfections

H1299, U2OS, 293, HeLa cells were maintained in DMEM medium supplemented with 10% fetal bovine serum. H1299 and 293 cells were transfected with plasmid DNA using the calcium phosphate protocol. U2OS cells were transfected with siRNA duplexes by Lipofectamine2000 (Invitrogen) according to the manufacturer's protocol.

In Vitro Deacetylation Assays

In Vitro Deacetylation Assays were performed as previously described (Luo et al. 2001, Cell, 107: 137-148). Purified acetylated p53 was incubated with purified SIRT1 and DBC-1 as indicated at 30° C. for 1 hour in the presence of 50 µM NAD. Reactions were performed in a buffer containing 50 mM Tris HCl (pH 9.0), 50 mM NaCl, 4 mM MgCl2, 0.5 mM DTT, 0.2 mM PMSF, 0.02% NP-40, and 5% glycerol. The reactions were resolved on SDS-PAGE and analyzed by Western blot using antibodies specific for acetylated p53 (Luo et al., 2000), total p53 (DO-1, sc-126, Santa Cruz), Sir2-CT (Luo, et al. 2001) and DBC-1 (Bethyl, BL1924).

Purification of Flag-Tagged Proteins

Cells were transfected with Flag-tagged expression constructs for p53, SIRT1 and DBC1 using the Calcium Phosphate Method as previously described. To immunoprecipitate the ectopically expressed FLAG-tagged proteins, transfected cells were lysed 24 hours post transfection in Flag-lysis buffer (50 mM Tris-HCl pH 7.9, 137 mM NaCl, 10 mM NaF, 1 mM EDTA, 1% Triton X-100, 0.2% Sarkosyl, 10% glycerol, and fresh proteinase inhibitor cocktail (SIGMA)) or for high stringency in BC500 (20 mM Tris pH7.9, 500 mM NaCl, 10% glycerol, 0.2 mM EDTA, 0.5% Triton X-100, and fresh proteinase inhibitor cocktail). The whole cell extracts were immunoprecipitated with the monoclonal anti-Flag antibody-conjugated M2 agarose beads (Sigma) at 4° C. overnight. After three washes with either BC500 or Flag-lysis buffer, followed by two washes with BC100 (20 mM Tris pH7.9, 100 mM NaCl, 10% glycerol, 0.2 mM EDTA, 0.1% Triton X-100), the bound proteins were eluted using Flag-Peptide (Sigma)/BC100 for 3 hours at 4° C. The eluted material was resolved by SDS-PAGE and detected by antibodies as indicated. For analysis of the SIRT1 complex, 50 µl of M2-eluted F-SIRT1 containing approximately 12.5 µg of total purified F-SIRT1 were fractionated by size exclusion chromatography on a Sepherose 12 Column on the SMART System (GE Healthcare) according to manufacturer's protocol.

GST-Pull-Down pCIN4-DBC1 or pCIN4-SIRT1 were labeled by incorporation of $^{35}$S-Methionine during in vitro translation (TNT Coupled Reticulocyte Lysate System, Promega Corporation).

5 ul of $^{35}$S-labeled protein was incubated with 3 µg of the purified GST protein fragments as indicated in the presence of 0.2% BSA in BC100 on a rotator overnight at 4° C. The proteins were pulled down using GST beads and the beads were washed five times with BC100 before elution with 50 ul of BC100 plus 20 mM reduced glutathione for 2 hours with gentle rotation. Eluted materials were resolved on SDS-PAGE and the presence of $^{35}$S-labeled protein was detected by autoradiography and the levels of the GST proteins by Coomassie stain.

siRNA-Mediated Ablation of DBC1, SIRT1 and p53

The ablation of DBC1 was performed by transfection of the U2OS cells with either of two siRNA duplex oligos (DBC1-RNAi#1: 5' CAGCGGGUCUUCACUGGUAUU 3' (SEQ ID NO:3) or DBC1-RNAi#2: 5'CAGCUUGCAUGAC-UACUUU3' (synthesized by Dharmacon) (SEQ ID NO:4)), which covered mRNA regions 582-602 nt (55-61aa) and 326-344 nt (64-69aa) of DBC1 respectively, by using Lipofectamine2000 according to the manufacture's protocol. SIRT1 RNAi (SiGenome Smartpool M-003540-01 (Dharmacon)), p53 RNAi (SiGenome Smartpool M-003329-01-0010 (Dharmacon)) and Control RNAi (On-target plus siControl non-targeting pool D-001810-10-20 (Dharmacon)) were used and transfected according to the manufacturers guidelines.

Luciferase Reporter Gene Assay

H1299 cells were transfected at 70% confluence in 6-well plates with plasmid DNA as indicated in the relevant figures. After 24 hours of incubation, cells were then harvested and the luciferase activity was measured using the Dual Luciferase Reporter Assay System Kit from Promega according the manufacturer's protocol.

In Vitro Acetylation Assay.

In vitro acetylation assays were performed as described previously (Gu, 1997; Luo, 2000)

Immunofluorescent Staining

Cells were fixed with 4% paraformaldehyde for 20 min on ice, rehydrated for 5 min in serum-free DMEM, and permeabilized with 0.2% Triton X-100 (Fisher) for 10 min on ice. Cells were incubated in 1% bovine serum albumin (BSA) (Sigma)/phosphate buffered salt solution (PBS) (Cellgro) for 30 min. Primary antibodies (as indicated) were added in 1% BSA/PBS for 45 min at room temperature. After washing with 1% BSA/PBS, secondary antibodies were added and incubated for 30 min at room temperature. Finally, cells were counterstained with DAPI to visualize the nuclei essentially as described before.

Annexin V-FITC Staining

The apopotosis assay was performed using the BD-Bioscience Annexin V-FITC staining kit according to the manufacturer's protocol.

Example 5

Transgenic Sir2 Mouse

In mouse, Sir2 is widely expressed in most cells, with the highest expression observed in germ cell, such as spermatocytes, although there are few exceptions such as sertoli cells in testis, which are nondividing and have minimal or undetectable levels of Sir2 protein (McBurney, 2003). It has been shown that Sir2 promotes proliferation and supports dividing cells and subsequently, increase of Sir2 expression leads to extension of life span. On the contrary, Other studies also have shown that Sir2 actually shortened life span in non-dividing cells (Fabrizio, 2005; Longo, 2006). So it is intriguing to investigate the role of Sir2 in controlling life span in a mouse.

Based on these studies, it is critical to faithfully overexpress Sir2 in order to investigate the role of Sir2 in controlling life span in a mouse, particularly the expression pattern of the transgene has to be the same as the endogenous Sir2 to avoid the detrimental effects of ectopic expression of Sir2 in non dividing cells.

Generation of BAC Containing Sir2

The sir 2 gene is approximately 30 kilobases (kb) and is located in the middle of the bacterial artificial chromosome (BAC), which is approximately 190 kb. It is likely that the BAC clone is large enough to contain all regulatory elements to ensure correct expression pattern of Sir2. In addition, the clone does not contain other full length known genes which might complicate the interpretation of phenotypes. To facilitate the detection of the transgene, an HA-Flag tag was inserted in the 3' end of the gene just before the stop codon, as well as a HindIII restriction endonuclease site to distinguish the transgene from the endogenous sir2 gene (FIG. 18A).

Genotyping

The Sir2 transgenic mice can be identified by Southern blotting using a 3' probe amplified using primers, 5' GTA-CATTCAACACTGTTGGTT 3' (SEQ ID NO: 5) and 5' CAAGGCTAACACCTTGGGATA 3' (SEQ ID NO:6). The probe will recognize a 1.5 kb HindIII band from the endogenous Sir2 locus and a 1 kb HindIII band from the BAC transgene. Both bands can be detected in transgenic mice and the ratio between the intensity of the two bands determined by the copy number of the transgene. In transgenic mice, there are two copies of endogenous Sir2 gene and 3 copies of transgene (FIG. 18B). Genotyping can also be done by PCR using primers, 5'TGGAGGGGATCAAGAGGTTGTTAA 3' (SEQ ID NO: 7) and 5' CCAAGAAGACAATCTATTTTC-CAG 3' (SEQ ID NO:8), which amplified an endogenous band of 230 base pairs (bps), as well as a transgenic band of 300 bps in transgenic mice (FIG. 18C).

Western Blotting

Sir2 protein is expressed from the transgene as shown by western blot (FIG. 19). Using anti-HA polyclonal antibody, HA and Flag tagged Sir2 protein can be detected only in cell extracts made from transgenic mice, but not in the extracts from wildtype non transgenic mice (FIG. 19A). Furthermore, using anti-Sir2 polyclonal antibody, two to three-fold higher expression levels of Sir2 can be detected in all tissues than that from the same tissues of nno-transgenic mice, demonstrating that increasing the copy number of the sir@ gene resulted in higher expression level of Sir2 protein in the transgenic mice (FIG. 19B).

Immunohistochemistry

Figure 20:
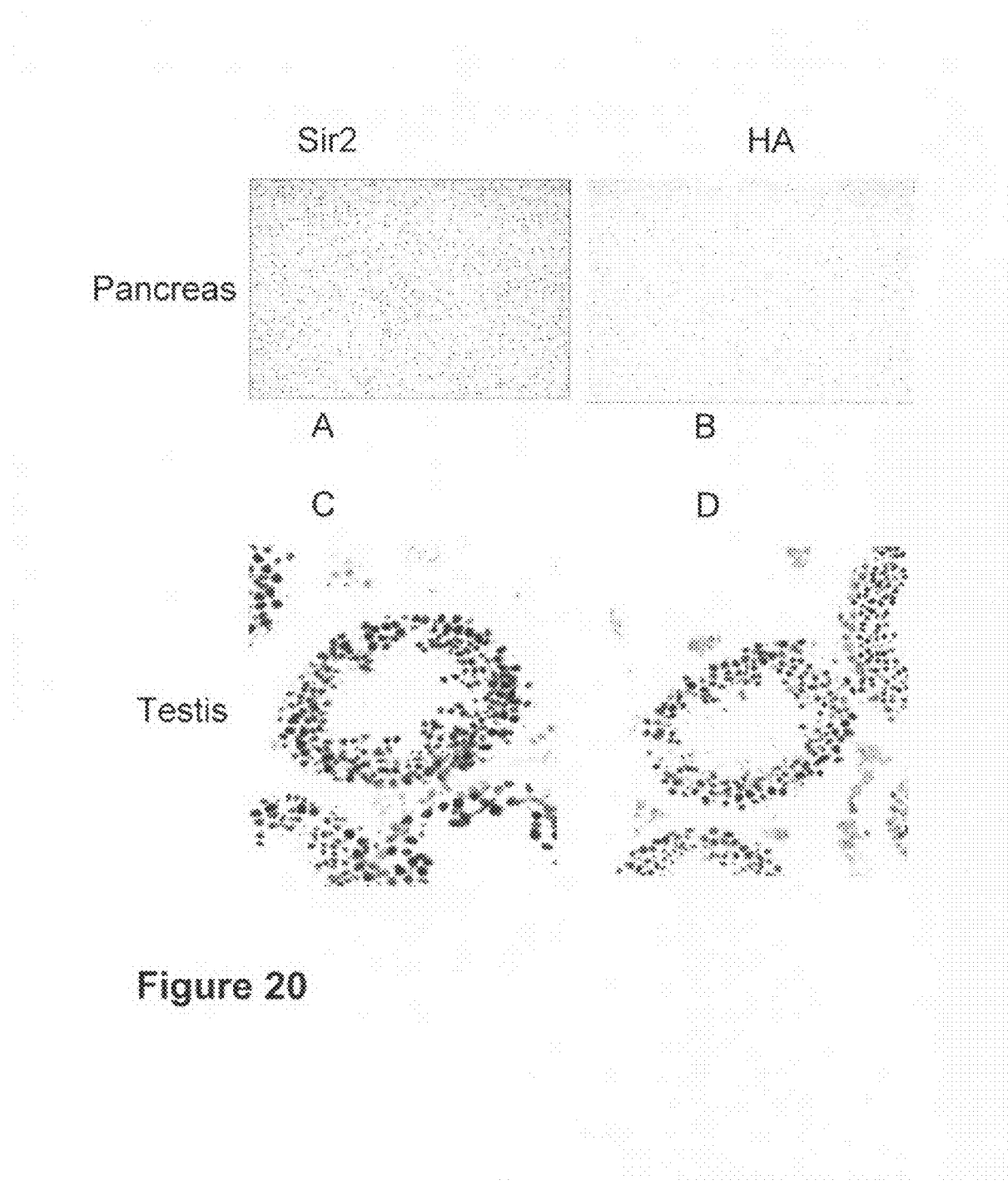
FIG. 20. Verification of Expression Pattern of Sir2 From the Transgene. (a) Anti-Sir2 antibody staining of pancreatic tissue from Sir2 transgenic mice (b) Anti-HA antibody staining of pancreatic tissue from Sir2 transgenic mice (c) Anti-Sir2 antibody staining of testis from Sir2 transgenic mice (d) Anti-HA antibody staining of testis from Sir2 transgenic mice.

To verify the expression pattern of sir2 from the transgene, major tissues from non-transgenic and transgenic mice were collected, fixed embedded in paraffin, sectioned, analyzed side by side using standard immunohistochemical methods. Sir2 expression pattern was determined by staining using either anti-HA antibody or anti-Sir2 antibody. Using anti-HA antibody, only the nuclei of the cells from transgenic mice showed staining, as indicated by the appearance of brown coloring, but not in the cells from non-transgenic mice (FIGS. 20B and 20D). The same expression pattern was observed when using either anti-Sir2 antibody or anti-HA antibody in most tissues (FIGS. 20A and 20B). However, although Sir2 is expressed strongly in spermatocytes (SP) in testis, it is not expressed in Sertoli cells (SE) in testis (FIG. 20C and McBurney, 2003). The same expression pattern of the Sir2 transgene was shown in testis as determined by immunostaining with anti-HA antibody (FIG. 20D).

Figure 22:
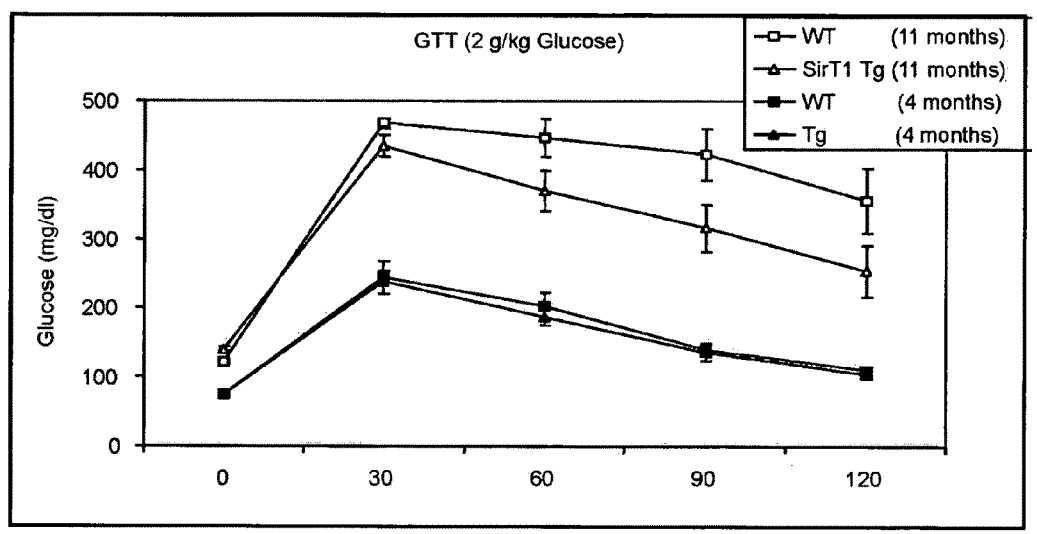
FIG. 22 shows that no significant difference could be observed in glucose tolerance tests performed on age matched cohorts of non-transgenic mice and Sir2 transgenic mice at 4-months old (closed triangle and closed square, respectively) but the same cohort of mice showed dramatic difference in the glucose tolerance tests at 11-months old (open triangle and open square)

The Sir2 BAC transgenic mice did not show any significant difference in total body mass and percent body fat composition (FIG. 21A). No significant difference was observed for internal organs (FIG. 21B). Because of the potential regulation of Foxo transcription factor by Sir2, and subsequent influence on metabolism and homeostasis, glucose tolerance test (GTT) was performed on the same age matched cohorts of non-transgenic and Sir2 transgenic mice when they were 4-months old and 11-months old. No significant difference was observed in the 4-moth old mice (FIG. 22, closed triangle and closed square), the same cohort of mice showed a dramatic difference by GTT at 11-moths old (FIG. 22, open triangle and open square). Compared to the non-transgenic mice, the Sir2 transgenic mice showed higher ability to clear out the blood glucose as indicated by the greater decrease of blood glucose level at the end of the GTT experiment. The results suggest that the transgenic mice maintain a 'younger' metabolic system compared to non-transgenic mice of the same age.

The detailed analysis revealed the better GTT performance could potentially be due to higher liver insulin sensitivities (FIG. 23A). Insulin stimulated inhibition of hepatic glucose production is greater in Sir2 transgenic mice than non-transgenic mice, 80% reduction versus 50% reduction (p=0.02). In addition, glucose infusion rate is much higher in Sir2 transgenic mice as compared to non-transgenic mice. The rate of whole-body glucose utilization by Sir2 transgenic mice is almost three-fold of non-transgenic mice (FIG. 23B).

The expression of SIR2 in transgenic mouse mimics the condition where the native inhibitor of SIRT1, DBC1, is inactive or the complexation between SIRT1 and DBC1 is inhibited. The Sir2 transgenic mouse model can be used to further study inhibitors of SIRT1 activity.

CONCLUSIONS

DBC1 has been identified as a specific inhibitor of SIRT1 activity in human cells. SIRT1 has been well accepted as a key modulator in a number of biological processes, including the stress response, cell metabolism and aging and the deacetylase activity of SIRT1 is essential for its mediated effects (Bordone, 2005; North, 2004; Baur, 2006). Thus, regulation of its enzymatic activity is of intense interest but largely unknown. By using p53 as a bona fide substrate of SIRT1 (Luo, 2001; Langley, 2002; Vaziri, 2001), we demonstrate that DBC1 enhances p53 acetylation levels and promotes p53-dependent apoptosis through repression of SIRT1 activity. Loss of DBC1 expression is observed in breast carcinomas and other tumor types (Hamaguchi, 2002; Sundararajan, 2005, Kurimoto, 2001; Martinez-CLiment, 2001; Swalwell, 2002), suggesting DBC1 as a putative tumor suppressor. However, the role of DBC1 loss in tumorigenesis remains unclear and is also complicated by loss of another gene called DBC2 in these tumors 9Hamaguchi, 2002; Knowles, 2005). While DBC1 regulation of SIRT1 is likely to influence other p53-independent processes (Motta, 2004; Brunet, 2004; Kitamura, 2005; Cheng, 2003; Chen, 2005; Yeung, 2004; Greene, 2004; Rodgers, 2005; Cohen, 2004), the data herein indicates that DBC1 has the potential to suppress tumor formation, at least in part, by enhancing p53 function. Further, the generation of a Sir2 transgenic mouse enables the study of SIRT1 inhibitors which have the potential stimulate p53 function.

REFERENCES

1. Ausubel, F. et al. eds., (1999) *Current Protocols in Molecular Biology*, J. Wiley: New York)
2. Baur, J. A. & Sinclair, D. A. Therapeutic potential of Resveratrol: the in vivo evidence. *Nat Rev Drug Discov* 5, 493-506 (2006).
3. Baur, J. A. et al. Resveratrol improves health and survival of mice on high-calorie diet. *Nature,* 444, 337-342 (2006).
4. Berdichevsky, A., Viswanathan, M., Horvitz, H. R. & Guarente, L. *C. elegans* SIR-2.1 interacts with 14-3-3 proteins to activate DAF-16 and extend life span. *Cell* 125, 1165-77 (2006).
5. Bordone, L. & Guarente, L. Calorie restriction, SIRT1 and metabolism: understanding longevity. *Nat Rev Mol Cell Biol* 6, 298-305 (2005).
6. Bordone, L., et al. SIRT1 regulates insulin secretion by repressing UCP2 in pancreatic beta cells. *PLoS Biol.* 4(2): e31.
7. Borra, M. T., Smith, B. C. & Denu, J. M. Mechanism of human SIRT1 activation by resveratrol. *J Biol Chem* 280, 17187-95 (2005).
8. Brunet, A. et al. Stress-dependent regulation of FOXO transcription factors by the SIRT1 deacetylase. *Science* 303, 2011-5 (2004).
9. Chen, W. Y. et al. Tumor suppressor HIC1 directly regulates SIRT1 to modulate p53-dependent DNA-damage responses. *Cell* 123, 437-48 (2005).
10. Chen, D., et al., Increase in activity during calorie restriction requires SIRT1. *Science* 310, 1641 (2005).
11. Cheng, H. L. et al. Developmental defects and p53 hyperacetylation in Sir2 homolog (SIRT1)-deficient mice. *Proc Natl Acad Sci USA* 100, 10794-9 (2003).
12. Cohen, H. Y. et al. Calorie restriction promotes mammalian cell survival by inducing the SIRT1 deacetylase. *Science* 305, 390-392 (2004).
13. Cohen, H. Y. et al. Acetylation of the C terminus of Ku70 by CBP and PCAF controls Bax-mediated apoptosis. *Mol Cell* 13, 627-38 (2004).
14. Dai, W. et al. PRK, a cell cycle gene localized to 8p21, is downregulated in head and neck cancer. *Genes Chromosomes Cancer* 27, 332-6 (2000).
15. Fabrizio, P., et al. Sir2 blocks extreme life-span extension. *Cell* 123, 655-67 (2005).
16. Fields, S. and Sternglanz, R. (1994) *Trends Genet.* 10(8): 286-92
17. Greene, W. C. & Chen, L. F. Regulation of NF-kappaB action by reversible acetylation. *Novartis Found Symp* 259, 208-17; discussion 218-25 (2004).
18. Gu, W., and Roeder, R. G. Activation of p53 sequence-specific DNA binding by acetylation of the p53 C-terminal domain. *Cell* 90, 595-606 (1997).
19. Guarente L. Sir2 links chromatin silencing, metabolism, and aging. *Genes Dev.* 14, 1021-6 (2002).
20. Hamaguchi, M. et al. DBC2, a candidate for a tumor suppressor gene involved in breast cancer. *Proc Natl Acad Sci USA* 99, 13647-52 (2002).
21. Heltweg, B. et al. Antitumor activity of a small-molecule inhibitor of human silent information regulator 2 enzymes. *Cancer Res* 66, 4368-77 (2006).
22. Howitz, K. T. et al. Small molecule activators of SIRTuins extend *Saccharomyces cerevisiae* lifespan. *Nature* 425, 191-6 (2003).
23. Huber, W. and Mueller, F. *Curr Pharm Des.* 12, 3999-4021 2006.
24. Kaeberlein, M. et al. The SIR2/3/4 complex and SIR2 alone promote longevity in *Saccharomyces cerevisiae* by two different mechanisms. *Genes Dev.* 13, 2570-80 (1999)
25. Kaeberlein, M. et al. Substrate-specific activation of SIR-Tuins by resveratrol. *J Biol Chem* 280, 17038-45 (2005).
26. Kitamura, Y. I. et al. FoxO1 protects against pancreatic beta cell failure through NeuroD and MafA induction. *Cell Metab* 2, 153-63 (2005).
27. Knowles, M. A., Aveyard, J. S., Taylor, C. F., Harnden, P. & Bass, S. Mutation analysis of the 8p candidate tumour suppressor genes DBC2 (RHOBTB2) and LZTS1 in bladder cancer. *Cancer Lett* 225, 121-30 (2005).

28. Kurimoto, F. et al. Unchanged frequency of loss of heterozygosity and size of the deleted region at 8p21-23 during metastasis of lung cancer. *Int J Mol Med* 8, 89-93 (2001).
29. Lagouge, M. et al. Resveratrol improves mitochondrial function and protects against metabolic disease by activating SIRT1 and PGC-1alpha. *Cell* 127, 1109-22 (2006).
30. Lakowicz et al., U.S. Pat. No. 5,631,169
31. Lambertson, et al., U.S. Pat. No. 6,562,576
32. Langley, E. et al. Human SIR2 deacetylates p53 and antagonizes PML/p53-induced cellular senescence. *Embo J* 21, 2383-96 (2002).
33. Longo, V. D., et al. SIRTuins in aging and age-related disease. *Cell* 126, 257-68 (2006).
34. Luo, J. et al. Negative control of p53 by Sir2alpha promotes cell survival under stress. *Cell* 107, 137-48 (2001).
35. Luo, J, Su, F., Chen, D., Shiloh, A., and Gu, W. Deacetylation of p53 modulates its effect on cell growth and apoptosis. *Nature* 408, 377-381 (2000).
36. Mai, A. et al. Design, synthesis, and biological evaluation of SIRTinol analogues as class III histone/protein deacetylase (SIRTuin) inhibitors. *J Med Chem* 48, 7789-95 (2005).
37. Martinez-Climent, J. A. et al. Loss of a novel tumor suppressor gene locus at chromosome 8p is associated with leukemic mantle cell lymphoma. *Blood* 98, 3479-82 (2001).
38. McBurney, M. W., et al. The mammalian SIR2alpha protein has a role in embryogenesis and gametogenesis. *Mol Biol Cell* 23, 38-54 (2003).
39. Motta, M. C. et al. Mammalian SIRT1 represses forkhead transcription factors. *Cell* 116, 551-63 (2004).
40. Napper, A. D. et al. Discovery of indoles as potent and selective inhibitors of the deacetylase SIRT1. *J Med Chem* 48, 8045-54 (2005).
41. Nayagam, V. M., et al., (2006) *Journal of Biomolecular Screening* 11(8):959-967
42. North, B. J., Marshall, B. L., Borra, M. T., Denu, J. M. & Verdin, E. The human Sir2 ortholog, SIRT2, is an NAD+-dependent tubulin deacetylase. *Mol Cell* 11, 437-44 (2003).
43. North, B. J. & Verdin, E. SIRTuins: Sir2-related NAD-dependent protein deacetylases. *Genome Biol* 5, 224 (2004).
44. Olaharski, A. J. et al. The flavoring agent dihydrocoumarin reverses epigenetic silencing and inhibits SIRTuin deacetylases. *PLoS Genet* 1, e77 (2005).
45. Picard, F. et al. SIRT1 promotes fat mobilization in white adipocytes by repressing PPAR-gamma. *Nature* 429, 771-776 (2004).
46. Rivas, G., and Minton A. P., (1993) *Trends Biochem Sci* 18, 284-287.
47. Rodgers, J. T. et al. Nutrient control of glucose homeostasis through a complex of PGC-1alpha and SIRT1. *Nature* 434, 113-8 (2005).
48. Rogina, B. and Halfand, S. L. Sir2 mediates longevity in the fly through a pathway related to calorie restriction. *Proc Natl Acad Sci USA* 101, 15998-16003.
49. Stavrianopoulos, et al., U.S. Pat. No. 4,868,103
50. Su, H. C., et al. A red wine antioxidant, possesses an insulin-like effect in streptozotocin-induced diabetic rats. *Am. J. Physiol. Endocrinol. Metab.* 24 Jan. 2006 (epub ahead of print).
51. Sundararajan, R., Chen, G., Mukherjee, C. & White, E. Caspase-dependent processing activates the proapoptotic activity of deleted in breast cancer-1 during tumor necrosis factor-alpha-mediated death signaling. *Oncogene* 24, 4908-20 (2005).
52. Swalwell, J. I. et al. Determination of a minimal deletion interval on chromosome band 8p21 in sporadic prostate cancer. *Genes Chromosomes Cancer* 33, 201-5 (2002).
53. Tang, B. L. and Chua C E. SIRT1 and neuronal diseases. *Mol Aspects Med* 16 Feb. 2007 (epub ahead of print).
54. Tissembaum, H A, Guarente, L. Increased dosage of a sir-2 gene extends lifespan in *Caenorhabditis elegans*. *Nature* 410, 227-30 (2001).
55. Vaziri, H. et al. hSIR2 (SIRT1) functions as an NAD-dependent p53 deacetylase. *Cell* 107, 149-59 (2001).
56. Viswanathan, M., Kim, S. K., Berdichevsky, A. & Guarente, L. A role for SIR2.1 regulation of ER stress response genes in determining *C. elegans* life span. *Dev Cell* 9, 605-15 (2005).
57. Yeung, F. et al. Modulation of NF-kappaB-dependent transcription and cell survival by the SIRT1 deacetylase. *Embo J* 23, 2369-80 (2004)

What is claimed is:

1. A method for identifying an agent which inhibits the complexation between DBC1 and SIRT1 comprising:
   (a) providing a first composition comprising an amount of DBC1 bound to SIRT1 and a control composition comprising the same amount of DBC1 bound to SIRT1 as the first composition;
   (b) contacting the first composition with a test agent;
   (c) determining i) the level of unbound SIRT in the first composition and the control composition or ii) the level of complexation between SIRT1 and DBC1 in the first composition and the control composition; and
   (d) determining i) the difference in the level of unbound SIRT1 in the first composition compared to the control composition or ii) the difference in the level of complexation between SIRT1 and DBC1 in the first composition compared to the control composition;
   wherein, if i) the level of unbound SIRT1 in the first composition is higher than the level of unbound SIRT1 in the control composition or ii) the level of complexation between SIRT1 and DBC1 in the first composition is lower than the level of complexation between SIRT1 and DBC1 in the control composition, then the test agent inhibits the complexation between SIRT1 and DBC1.

2. The method of claim 1, wherein step (b) is performed in vitro.

3. The method of claim 1, wherein the test agent is a peptide.

4. The method of claim 3, wherein the peptide can hybridize with DBC1 or SIRT1 under stringent conditions.

5. The method of claim 2, wherein the difference in the level of unbound SIRT1 or the difference in the level of complexation between SIRT1 and DBC1 is determined by differential centrifugation, chromatography, gel filtration chromatography, ion-exchange chromatography, electrophoresis, immunoprecipitation, pulldown assay, ELISA assays fluorescence energy transfer, surface plasmon resonance, or in vitro tubulin deacetylation assays.

6. The method of claim 1, wherein step (b) is performed on a cell.

7. The method of claim 1, wherein step (b) is performed inside a cell.

8. The method of claim 6, wherein step (b) is performed outside a cell and the test agent causes a cascade effect.

9. The method of claim 6, wherein the cell is a yeast cell.

10. The method of claim 6, wherein the cell is a human osteosarcoma U2OS cell.

11. The method of claim 6, wherein difference in the level of unbound SIRT1 or difference in the level of complexation between SIRT1 and DBC1 is determined by yeast two hybrid, adipoctye differentiation assay, or deacetylation assay.

* * * * *

SEQUENCE LISTING

```
<160> NUMBER OF SEQ ID NOS: 8

<210> SEQ ID NO 1
<211> LENGTH: 19
<212> TYPE: RNA
<213> ORGANISM: artificial sequence
<220> FEATURE:
<223> OTHER INFORMATION: siRNA directed to human DBC1 protein

<400> SEQUENCE: 1
cagcgggucu ucacuggua                                                  19

<210> SEQ ID NO 2
<211> LENGTH: 19
<212> TYPE: RNA
<213> ORGANISM: artificial sequence
<220> FEATURE:
<223> OTHER INFORMATION: siRNA directed to human DBC1 protein

<400> SEQUENCE: 2
cagcuugcau gacuacuuu                                                  19
```

```
<210> SEQ ID NO 3
<211> LENGTH: 21
<212> TYPE: RNA
<213> ORGANISM: artificial sequence
<220> FEATURE:
<223> OTHER INFORMATION: siRNA duplex oligonucleotide directed to human
      DBC1 protein

<400> SEQUENCE: 3
cagcgggucu ucacugguau u                                              21

<210> SEQ ID NO 4
<211> LENGTH: 19
<212> TYPE: RNA
<213> ORGANISM: artificial sequence
<220> FEATURE:
<223> OTHER INFORMATION: siRNA duplex oligonucleotide directed to human
      DBC1 protein

<400> SEQUENCE: 4
cagcuugcau gacuacuuu                                                 19

<210> SEQ ID NO 5
<211> LENGTH: 21
<212> TYPE: DNA
<213> ORGANISM: artificial sequence
<220> FEATURE:
<223> OTHER INFORMATION: primer directed to mouse Sir2

<400> SEQUENCE: 5
gtacattcaa cactgttggt t                                              21

<210> SEQ ID NO 6
<211> LENGTH: 21
<212> TYPE: DNA
<213> ORGANISM: artificial sequence
<220> FEATURE:
<223> OTHER INFORMATION: primer directed to mouse Sir2

<400> SEQUENCE: 6
caaggctaac accttgggat a                                              21

<210> SEQ ID NO 7
<211> LENGTH: 24
<212> TYPE: DNA
<213> ORGANISM: artificial sequence
<220> FEATURE:
<223> OTHER INFORMATION: primer directed to mouse Sir2

<400> SEQUENCE: 7
tggaggggat caagaggttg ttaa                                           24

<210> SEQ ID NO 8
<211> LENGTH: 24
<212> TYPE: DNA
<213> ORGANISM: artificial sequence
<220> FEATURE:
<223> OTHER INFORMATION: primer directed to mouse Sir2

<400> SEQUENCE: 8
ccaagaagac aatctatttt ccag                                           24
```